(12) United States Patent
Takaki et al.

(10) Patent No.: US 6,446,629 B1
(45) Date of Patent: Sep. 10, 2002

(54) ARTIFICIAL RESPIRATION APPARATUS

(75) Inventors: Toshihisa Takaki, Hamamatsu (JP);
Masatake Saito, Hamamatsu (JP);
Mikio Yasukawa, Hamamatsu (JP);
Yasuhito Sugiura, Hamamatsu (JP);
Katsuyoshi Suzuki, Hamamatsu (JP);
Masahiro Kamada, Hamamatsu (JP);
Tomohisa Ohtake, Hamamatsu (JP);
Yoshitsugu Yamada, 37-14, Daisawa 1-chome, Setagaya-ku, Tokyo (JP);
Kazufuku Nitta, Omiya (JP)

(73) Assignees: Suzuki Motor Corporation, Shizuoka (JP); Yoshitsugu Yamada, Tokyo (JP); Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/363,183

(22) Filed: Jul. 29, 1999

(30) Foreign Application Priority Data

Jul. 31, 1998 (JP) .......................................... 10-230099

(51) Int. Cl.⁷ .............................................. A61M 16/00
(52) U.S. Cl. ............................... 128/204.18; 128/205.24
(58) Field of Search ........................ 128/204.18, 204.21, 128/204.23, 204.24, 205.24, 205.18, 205.19; 137/907, 908

(56) References Cited

U.S. PATENT DOCUMENTS

| | | | | | |
|---|---|---|---|---|---|
| 4,463,756 A | * | 8/1984 | Thuc | ..................... | 128/204.21 |
| 4,543,951 A | * | 10/1985 | Phuc | ..................... | 128/204.25 |
| 5,542,416 A | * | 8/1996 | Chalvignac | ............ | 128/204.23 |
| RE35,339 E | * | 10/1996 | Rapoport | ................ | 128/204.18 |
| 5,683,232 A | * | 11/1997 | Adahan | ................. | 128/205.24 |
| 5,740,796 A | * | 4/1998 | Skog | ..................... | 128/204.23 |
| 5,752,506 A | * | 5/1998 | Richardson | ............ | 128/204.18 |
| 5,813,399 A | * | 9/1998 | Isaza et al. | ............. | 128/204.21 |
| 5,850,835 A | | 12/1998 | Takaki et al. | ........... | 128/204.18 |
| 6,000,396 A | * | 12/1999 | Melker et al. | .......... | 128/204.21 |
| 6,095,140 A | * | 8/2000 | Poon et al. | ............. | 128/204.26 |
| 6,155,252 A | * | 12/2000 | Warters | .................. | 128/200.24 |
| 6,230,708 B1 | * | 5/2001 | Radko | ................... | 128/205.24 |

* cited by examiner

*Primary Examiner*—John G. Weiss
*Assistant Examiner*—Teena Mitchell
(74) *Attorney, Agent, or Firm*—Greenblum & Bernstein P.L.C.

(57) ABSTRACT

The present invention provides an artificial respiration apparatus 12 of a high oscillation type, in which oxygen supply to a patient P and exhaled gas discharge are urged by an oscillating gas having a higher frequency than the cycle of the patient respiration. The apparatus includes a discharge direction regulating mechanism 7 for regulating the exhaled gas to flow only in the discharge direction.

15 Claims, 18 Drawing Sheets

FIG. 9
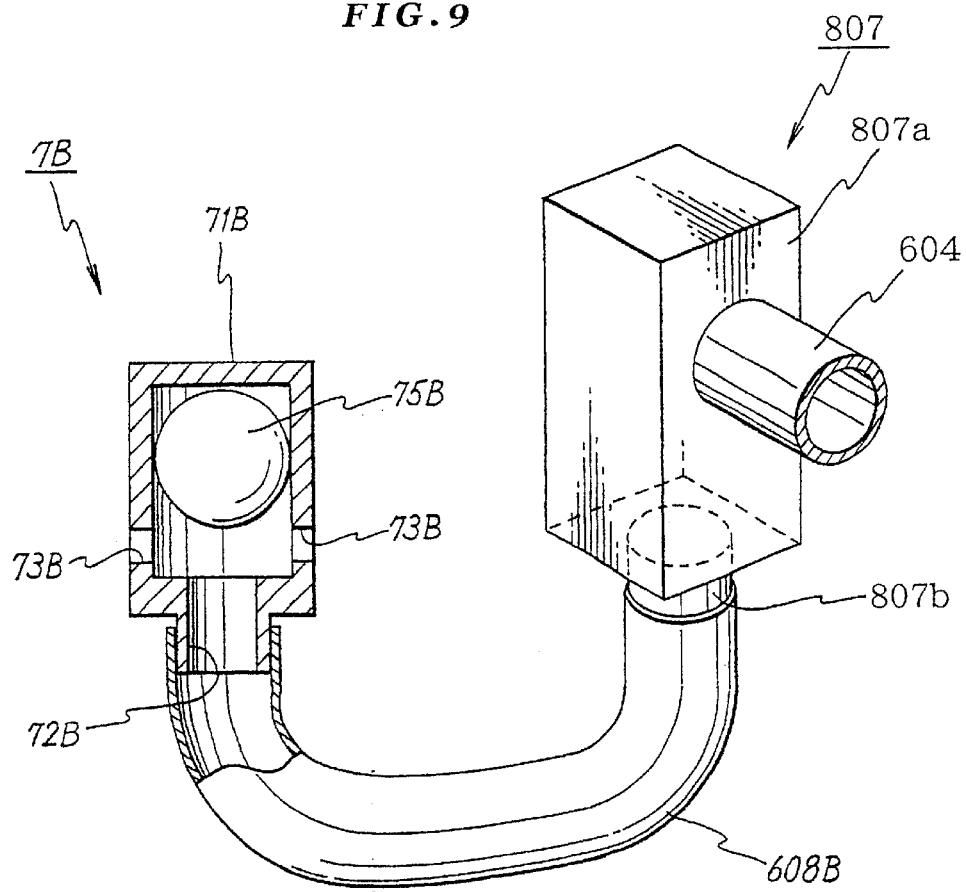
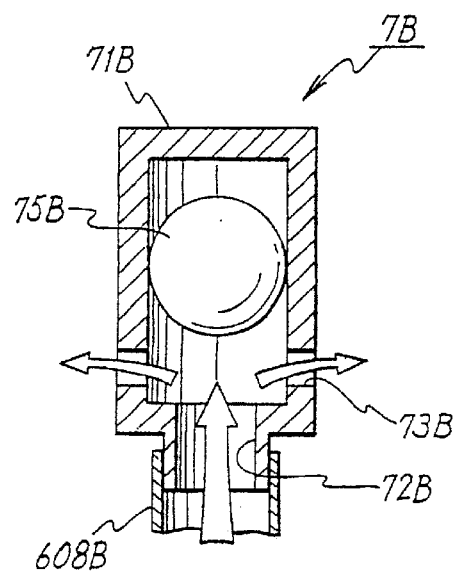
Fig 10(A)
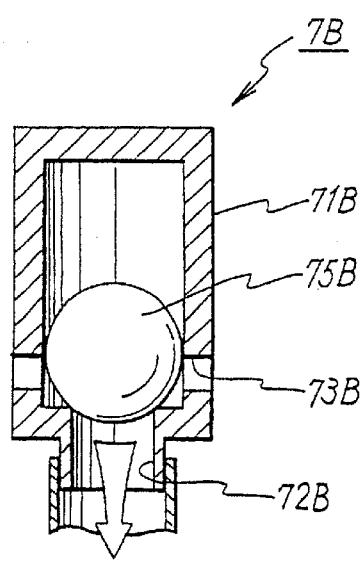
Fig 10(B)

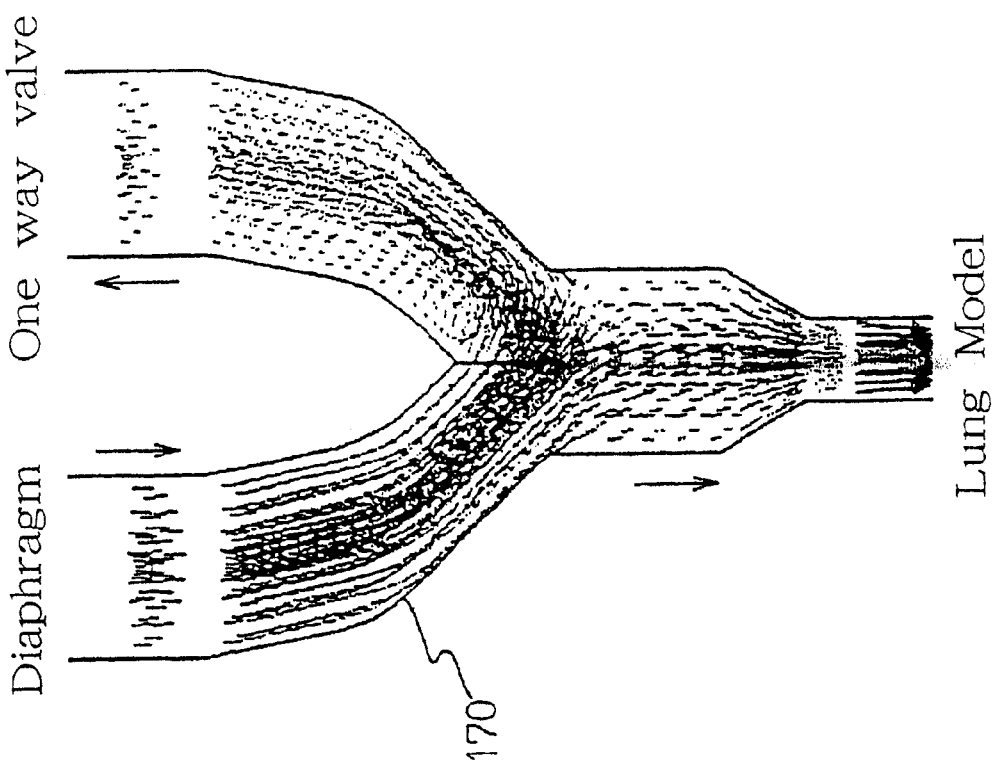
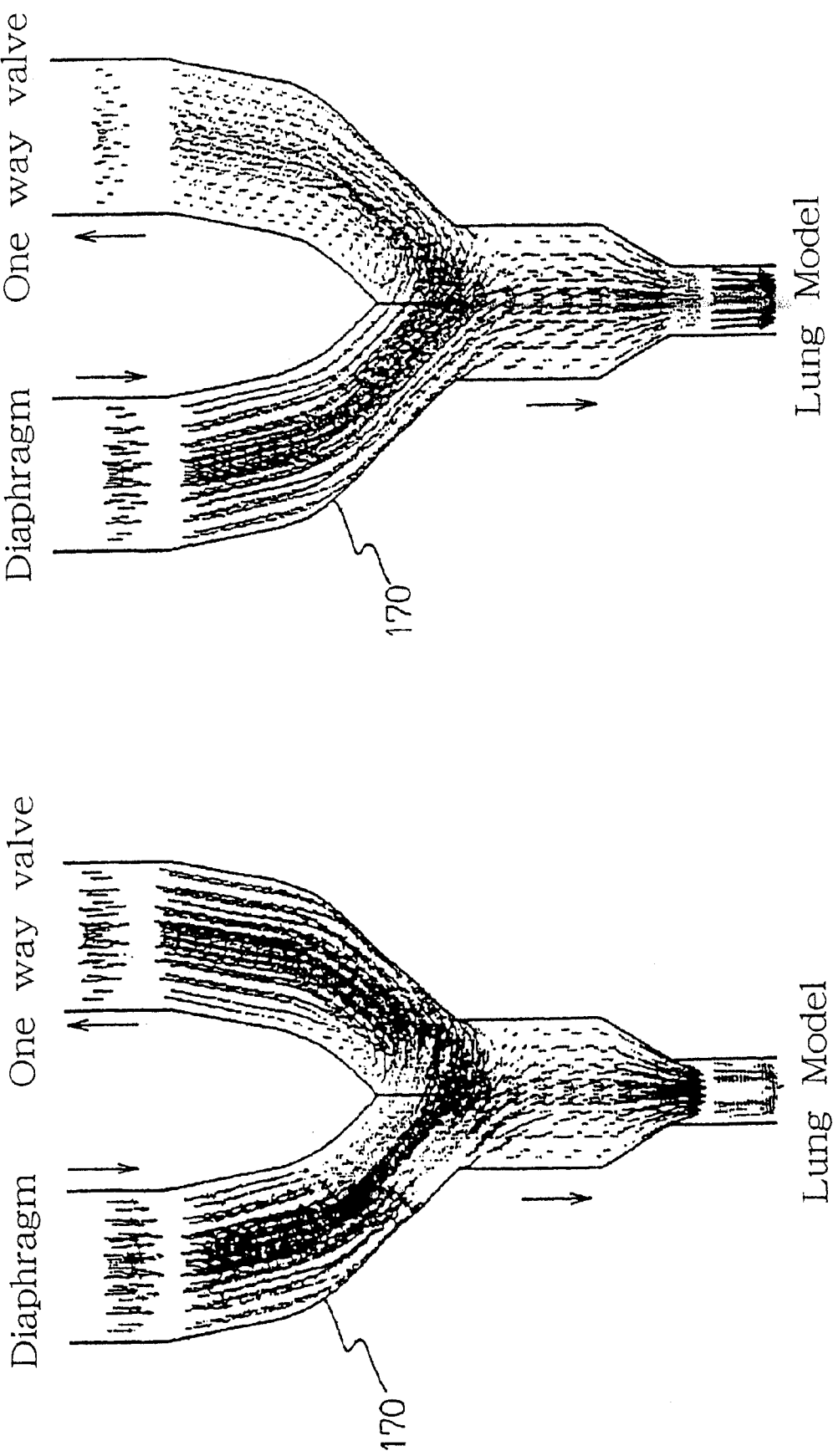
Fig 12 (A)
Fig 12 (B)

ARTIFICIAL RESPIRATION APPARATUS

BACKGROUND OF THE INVENTION

1. Field of the Invention

The present invention relates to an artificial respiration apparatus and in particular, to an artificial respiration apparatus of high-frequency oscillation type.

The conventional high-frequency oscillation type respiration apparatus includes three pipe routes 605, 604 and 623 which are connected to a three-way branched pipe 170 having: a patient side opening 171, oxygen supply opening 172, and a discharge opening 173. The patient opening 171 is connected to a patient. The oxygen supply opening 172 is connected to an oxygen supply port. The discharge opening 173 is connected to a discharge exit 607.

2. Description of the Related Art

FIG. 22 schematically shows a discharge route of a conventional respiration apparatus of high-frequency oscillation.

The conventional high-frequency oscillation type respiration apparatus includes three pipe routes 605, 604, and 623 which are connected to a three-way branched pipe 170 having: a patient side opening 171, oxygen supply opening 172, and a discharge opening 173. The patient opening 171 is connected to a patient. The oxygen supply opening 172 is connected to an oxygen supply port. The discharge opening 173 is connected to a discharge exit 807.

With the aforementioned configuration, oxygen is supplied from the oxygen supply port to the oxygen supply opening 172 in a state urged by oscillating pressure. The oxygen is supplied through the oxygen supply opening 172 to the patient side opening 171, reaching lungs of a patient P. On the other hand, carbon dioxide ($CO_2$) discharged from the lungs of the patient P passes through the patient side opening 171, the discharge valve 607 into the atmosphere.

Here, as shown in FIG. 23, the discharge exit 607 has: a casing 607a for introducing a discharge pipe 604 connected to the discharge opening 173; and a discharge port 607b for discharging the carbon dioxide.

However, in the aforementioned conventional apparatus, a negative pressure urging is also carried out so as to discharge carbon dioxide from the lungs of the patient P. Here, the exhaled gas from the patient P is urged into the three-way branched pipe 170. Simultaneously with this, atmospheric air intrudes from the discharge port 607b of the discharge exit as shown in FIG. 24. This results in reduction of the discharged respiration gas from the patient, i.e., reduction of the gas exchange at one cycle of the oscillating air pressure.

Moreover, in this high-frequency gas exchange, it is difficult, to control pressure inside the pipe route 604 so as to maintain an average in-pipe pressure (almost atmospheric pressure) lower than the conventional intermittent forced ventilation. Simultaneously with this, if an exhaled gas quantity is increased, the lowest value of the average in-pipe pressure is increased.

Moreover, in the conventional high-frequency oscillation type artificial respiration method, the in-pipe pressure between the patient and the discharge end has been maintained lower than the conventional intermittent type artificial respiration apparatus. However, when the average in-pipe pressure is set low such as almost atmospheric pressure, the atmospheric air intrudes from the discharge end, and it is difficult to obtain a target pressure. Simultaneously with this, if an exhaled gas amount is increased the average in-pipe pressure is increased.

SUMMARY OF THE INVENTION

It is therefore an object of the present invention to provide an artificial respiration apparatus capable of preventing intrusion of the atmospheric air from the discharge end so as to perform gas exchange more effectively.

BRIEF DESCRIPTION OF THE DRAWINGS

FIG. 5A shows operation at a positive pressure and FIG. 5B shows operation at a negative pressure.

FIG. 8A shows the valve at a positive pressure, and FIG. 8B shows the valve at a negative pressure.

FIG. 9 is a perspective view of still another example of the one-way valve partially exposed.

FIG. 10 is a cross sectional view of the one-way valve of FIG. 9. FIG. 10A shows the valve at a positive pressure, and FIG. 10B shows the valve at a negative pressure.

FIG. 12 shows a gas flow speed distribution in the three-way branched pipe at a positive pressure in the artificial respiration apparatus using the lung model. FIG. 12A shows a flow rate distribution when no one-way valve is used, and FIG. 12B shows a flow rate when a one-way valve is mounted.

FIG. 13A shows a flow rate distribution when no one-way valve is used, and FIG. 13B shows a flow rate when a one-way valve is mounted.

DESCRIPTION OF THE PREFERRED EMBODIMENTS

[Embodiment 1]

Description will now be directed to an artificial respiration apparatus according to a first embodiment of the present invention with reference to FIG. 1 to FIG. 6.

Figure 1:
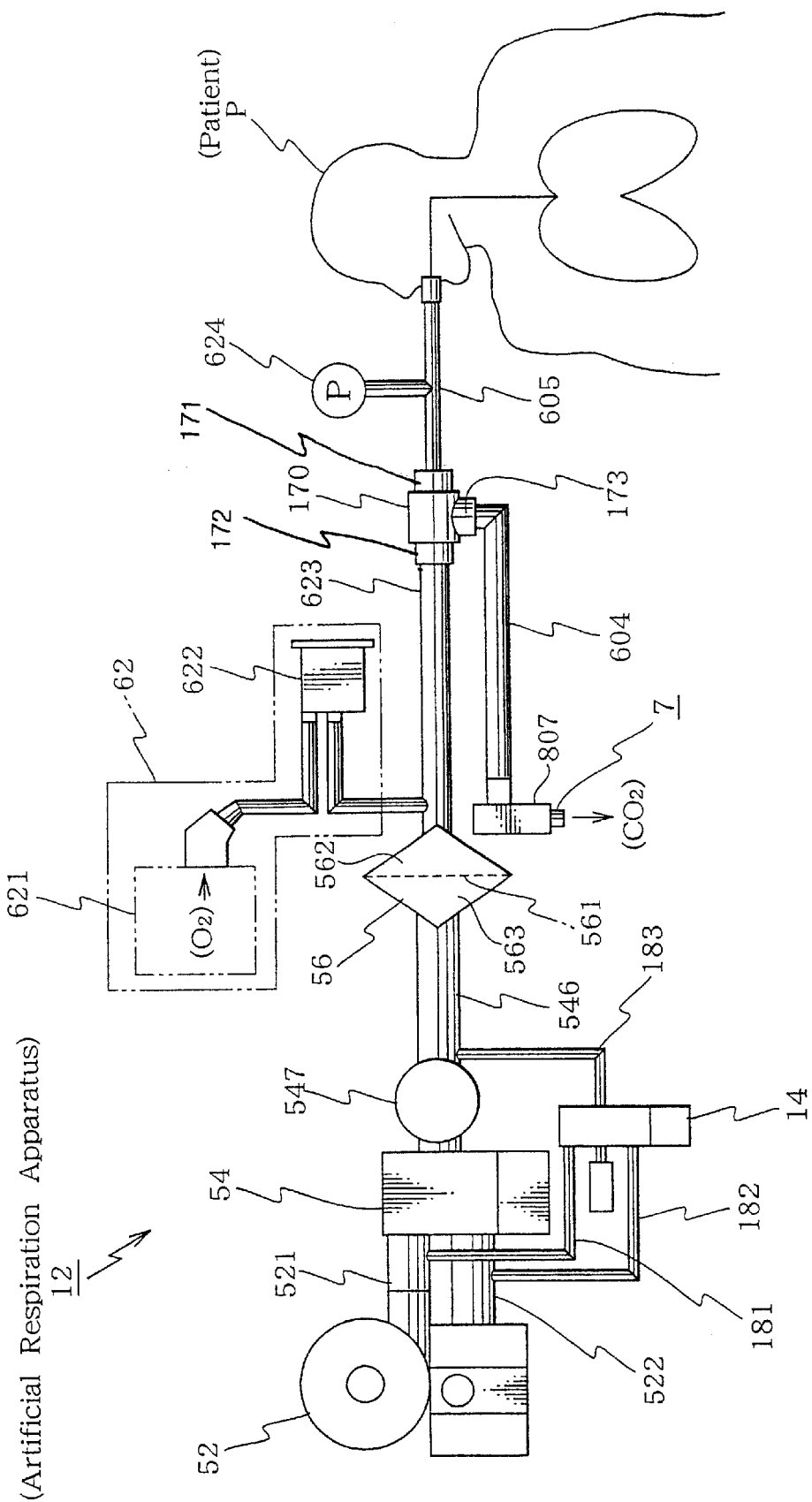
FIG. 1 shows configuration of an artificial respiration apparatus according to a first embodiment of the present invention.

FIG. 1 shows a basic configuration of an artificial respiration apparatus of high frequency oscillation type (HFO) according to the first embodiment. This HFO type artificial respiration apparatus uses a one-way valve serving as a discharge direction regulating mechanism so that the exhaled gas from a patient P goes only in a predetermined direction to be discharged into the atmosphere. It should be noted that like components as the aforementioned conventional example are indicated by like reference symbols and no redundant explanation will be given.

FIG. 1 is a block diagram showing the entire configuration of the HFO type artificial respiration apparatus including a control system according to the present invention.

The artificial respiration apparatus 12 comprises: an inhaling gas port 62 for supplying oxygen; a blower 52 for simultaneously generating a positive pressure Ap and a negative pressure An; a rotary valve mechanism 54 for alternatively selecting the positive pressure and the negative pressure generated by the blower 52 so as to be converted into a predetermined oscillating gas pressure Apn; a diaphragm mechanism 56 for applying an oscillating air pressure to a respiration gas (mixture of oxygen and air) supplied from an inhaling gas port 62 to a patient P; and a diaphragm neutral position control device 10.

The inhaling gas port 62 includes: a blender 621 for mixing oxygen with the open air; and a humidifier 622 for applying humidity to the air transmitted from the blender 621. The humidifier 622 is connected to an inhaling pipe 623 for supplying a humidified gas mixture Ai to the patient P. The inhaling pipe 623 has one end communicating with a pressurized chamber 563 and the other end communicating with the three-way branched pipe 170.

This three-way branched pipe 170 has three openings: patient side opening 171, the oxygen supply side opening 172, and exhaled gas discharge side opening 173. The oxygen supply side opening 172 is connected to the inhaling pipe 623. Moreover, the patient side opening 171 is connected to an inhaling pipe 605 reaching the patient P. On this inhaling pipe 605, there is provided a pressure sensor 624 for detecting an exhaling condition of the patient P.

Figure 3:
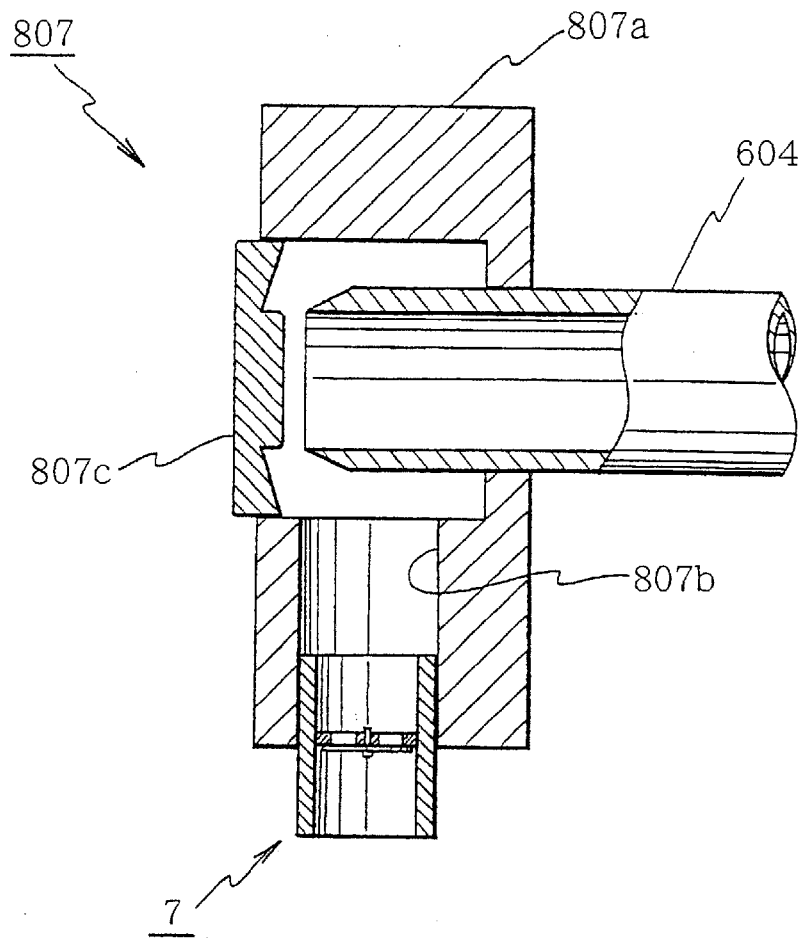
FIG. 3 is a cross sectional view of one-way valve shown in FIG. 1.

Furthermore, the exhaling gas discharge side opening 173 of the three-way branched pipe 170 is connected to one end of a discharge pipe 604 which is connected to a discharge valve 807, constituting a discharge route for the exhaled gas from the patient P. As shown in FIG. 3, the discharge valve 807 includes a gas discharge port 807b and a flow rate control electromagnetic valve (control silicon sheet) 807c. The aforementioned one-way valve 7 is mounted on the discharge port 807b. The flow rate through the electromagnetic valve 807c is controlled according to an output of the pressure sensor 624.

The blower 52 includes a positive pressure pipe 521 and a negative pressure pipe 522. Air is taken into the negative pressure pipe 522 and the air is discharged from the positive pressure pipe 521. This positive pressure pipe 521 is connected to an orifice pipe 524 communicating with the open air, and the negative pressure pipe 522 is connected to an orifice pipe 523.

The rotary valve mechanism 54 is constituted by a rotary valve 544 having ports 541, 542, and 543; and a drive block 545 for rotating the rotary valve 544. The drive block 545 includes a motor and reduction gears (not depicted) for rotating the rotary valve 544, for example, at 900 rpm. Each time the rotary valve 544 makes one turn the port 541 is made to communicate with the port 543, and subsequently the port 542 is made to communicate with the port 543. Thus, oxygen supply is urged with the oscillating air pressure Apn of frequency 15 Hz. Port 543 is connected to an oscillating air pressure pipe 546 for transmitting the oscillating air pressure Apn to the diaphragm mechanism 56. A flow rate control valve 547 is inserted into the oscillating air pressure pipe 546.

The diaphragm mechanism 56 includes a pressurizing chamber 562, pressurized chamber 563, and a diaphragm 561. The pressurizing chamber 562 is connected to the oscillating air pressure pipe 546.

Next, explanation will be given on the diaphragm neutral position control device 10 including: a diaphragm position sensor 601 for detecting the position of the diaphragm 561; a pressure control valve 14 pressure control mechanism) for controlling the positive pressure Ap, negative pressure An, and oscillating air pressure Apn; and a control block 16 for controlling a pressure control valve 14 according to the position of the diaphragm 561 detected by the diaphragm position sensor 601. The pressure control valve 14 is mechanically similar to the rotary valve. The control valve 14 includes: a main body 146 having ports 141 to 145; rotary member 149 arranged in the main body for connecting the ports 141, 142, 143, 144, and 145 with a predetermined combination; and an actuator 147 for rotating this rotary member 149 in a normal and reversed directions. The actuator is constituted by a motor and reduction gears and is capable of rotating the rotary member 149 with a desired angle.

The port 141 of the pressure control valve 14 is connected to a positive pressure bypass pipe 181. The port 142 is connected to a negative pressure bypass pipe 182 communicating with the negative pressure pipe 522. The port 143 is connected to an oscillating air pressure bypass pipe 183 communicating with the oscillating air pressure pipe 546. The ports 144 and 145 are connected to the open air ports 184 and 185, respectively.

The pressure control valve 14 is normally in a state that all the ports 141 to 145 are closed. The pressure control valve 14 is switched to state A (not shown) or state B (not shown) if the diaphragm 561 is in an abnormal position.

In state A, the port 141 is connected to the port 144, and the port 142 is connected to the port 143. In this case the port 145 is closed. In this state A, the absolute value of the positive pressure Ap generated by the blower 52 is reduced. Moreover, an oscillating air pressure Apn and a negative pressure An are simultaneously applied to the diaphragm 561.

In state B, the port 142 is connected to the port 145, and the port 141 is connected to the port 143. In this case the port 144 is closed. In this state B, the absolute value of the negative pressure An generated by the blower 52 is increase. Moreover, the oscillating air pressure Apn and a positive pressure Ap are simultaneously applied to the diaphragm 561.

The control block 16 includes a microcomputer (not shown) having a CPU, ROM, RAM, I/O interface (none of which are shown) for example. This control block is supplied with the information on operation of the diaphragm 561 obtained from the diaphragm position sensor and according to this information, detects a shift of the diaphragm 561 from its average neutral position. If the average neutral position of the diaphragm is changed, the control block 16 operates as follows.

When the neutral position of the diaphragm 561 is shifted toward the patient P (rightward in the figure), the pressure control valve 14 is switched to the state A. In this state A, an absolute value of the positive pressure Ap (not shown) generated by the blower 52 is reduced. Moreover, the oscillating air pressure Apn (not shown) is also lowered. Thus, the diaphragm 561 position is corrected to the center.

On the contrary when the neutral position of the diaphragm 561 is shifted toward the blower 52 (leftward in the figure), the pressure control valve 14 is switched to the state B. In this state B, the negative pressure An is increased, and the oscillating air pressure Apn is increased. Thus, the neutral position of the diaphragm is corrected to the center.

That is, correction of the neutral position of the diaphragm 561 can be performed rapidly and effectively because both of the positive pressure Ap and the negative pressure An are controlled together with the oscillating air pressure Apn instead of using the atmospheric air alone.

Next, explanation will be given on the one-way valve with reference to FIG. 3 to FIG. 5.

FIG. 3 is a cross sectional view of the one-way valve 7 mounted on the discharge valve 807. FIG. 4 is an exploded perspective view of the one-way valve 7. FIG. 5 explains operation of the one-way valve 7. This one-way valve 7 includes: a through hole forming body 71 having two cylindrical members 72a and 72b, and a partition 73 having through holes 73a for passing an exhaled gas; and a film-shaped valve member 75 which is seated in the vicinity of the through holes 73a to cover the through holes from the downstream side.

Figure 4:
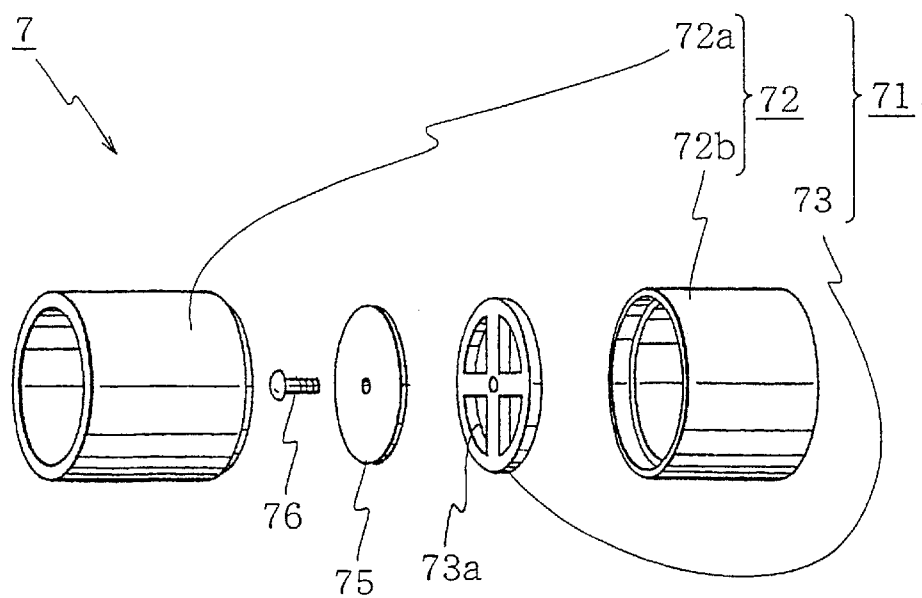
FIG. 4 is an exploded perspective view of the one-way valve of FIG. 3.
Figure 5:
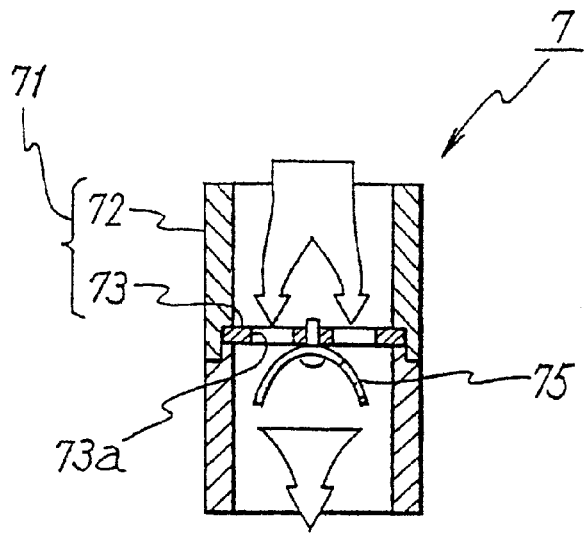
FIG. 5 shows operation of the one-way valve.
Figure 5:
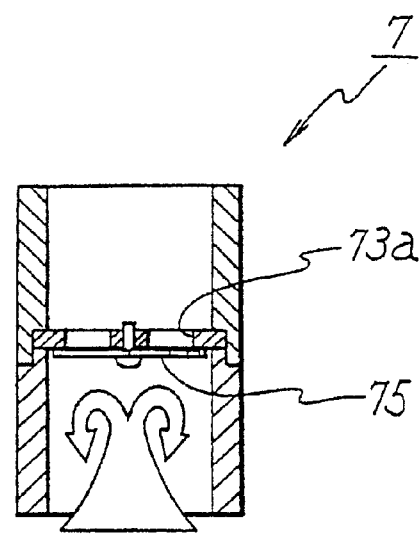

As shown in FIG. 4, the through hole forming body 71 is constituted by the two cylindrical members 72a and 72b connected to each other to constitute a single cylindrical body 72 and the partition 73 to separate an interior of the cylindrical body 72 into two parts (first part and a second part). The one-way valve 7 is mounted with the cylindrical body 72 inserted into the discharge port 807b of the discharge valve 807 (see FIG. 3). Moreover, the partition has four through holes 73a arranged around the center of the partition at an identical interval.

The valve member 75 having a high flexibility is seated on the downstream side of the partition 73. This valve member 75 has a disc shape having a diameter slightly smaller than the inner diameter of the cylindrical body 72 and fixed to the center of the partition by a pin 76. That is, this valve member covers all of the four through holes 73a.

In the one-way valve 7 having the aforementioned configuration, when a positive pressure is applied by the diaphragm mechanism 56, an inner pressure of the discharge valve 807 pushes the valve member 75 and an exhaled gas is discharged from the through holes 73a (FIG. 5A). On the contrary, when a negative pressure is applied, the valve member 75 is pushed to the partition 73 by the open air to cover the through holes 73a (FIG. 5B).

Next, explanation will be given on the operation of the artificial respiration apparatus 12 having the aforementioned configuration.

Firstly, a gas mixture (Ai) containing oxygen is supplied from the inhaling block and the blower 52 starts drive operation. The positive pressure Ap and the negative pressure An generated by the blower 52 is turned into an oscillating gas pressure Apn, which is fed to the diaphragm mechanism 56. In the diaphragm mechanism 56, the diaphragm 561 is oscillated by the cycle of the oscillating gas pressure Apn. The oscillation of the diaphragm 561 changes the pressure inside the inhaling pipe 623. With this positive pressure Ap of the oscillating gas pressure Apn, oxygen Ai is supplied to a patient P all the time. Moreover, with the negative pressure of the oscillating gas pressure Apn, exhaled gas containing carbon dioxide is pulled out from the lungs of the patient P into the three-way branched pipe 170 and discharged via the discharge opening 173 and the discharge pipe 604.

Here, the convex-concave movement of the diaphragm 561 is detected by the diaphragm position sensor 601, and a detected data is supplied to the control block 16. If the movement of the diaphragm is disturbed by spontaneous breathing, this information is promptly output to the control block 16. For example, when the center position of the diaphragm 561 is shifted toward the patient P (rightward in the FIG. 2), the control block 16 operates to switch the pressure control valve 14 to the state A, so that the center position of the diaphragm is corrected. Moreover, when the center position of the diaphragm 561 is shifted toward the blower 52 (leftward in FIG. 2), the control block operates to switch the pressure control valve 14 to the state B so as to correct the position;of the diaphragm 56. Thus, the diaphragm 561 is maintained at the center, enabling a stable respiration.

Figure 2:
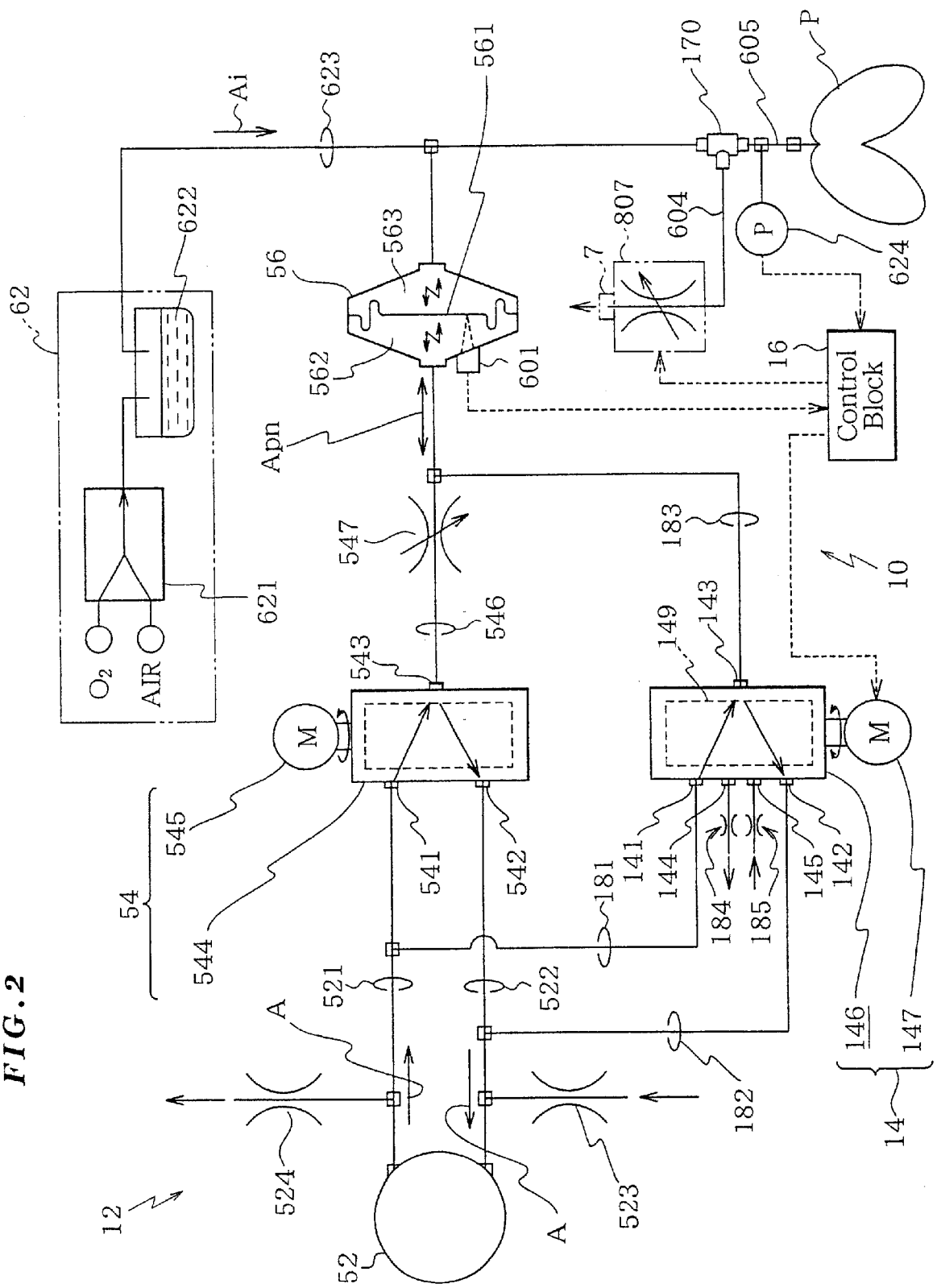
FIG. 2 is a block diagram showing components of the artificial respiration apparatus of the first embodiment.

Here, explanation will be given on the operation of exhaled gas discharge route with reference to FIG. 2, FIG. 3, and FIG. 5. Firstly, when a positive pressure Ap is applied from the diaphragm mechanism 56, the exhaled gas from the patient P is sent through the discharge pipe 604 (see FIG. 1) into the casing 807a of the discharge valve 807. This increases an inner pressure in the casing 807a and moves the valve member 75 downward so as to open the holes 73a (FIG. 5A). Thus the gas is discharged outside from the artificial respiration apparatus 12.

Moreover, when a negative pressure Pn is applied from the diaphragm mechanism 56, the inner pressure in the casing 807a of the discharge valve 807 is reduced. The valve member 75 is pushed to the partition 73 to close the through holes 73a. Thus, intrusion of the atmospheric air is prevented.

As has been described above, the present embodiment employs the aforementioned one-way valve in the discharge port 807b of the discharge valve 807. Accordingly, it is possible to prevent intrusion of the atmospheric air not only at a positive pressure but also at a negative pressure or the oscillating pressure. This prevents reverse flow of the exhaled gas, increasing the exhaled gas volume, i.e., gas exchange quantity per one cycle of the oscillation.

Moreover, because this artificial respiration apparatus prevents intrusion of the atmospheric air, it is easy to maintain an average pressure in the vicinity of the patients mouth (hereinafter, referred to as a mouse pressure) at a low level.

Figure 6:
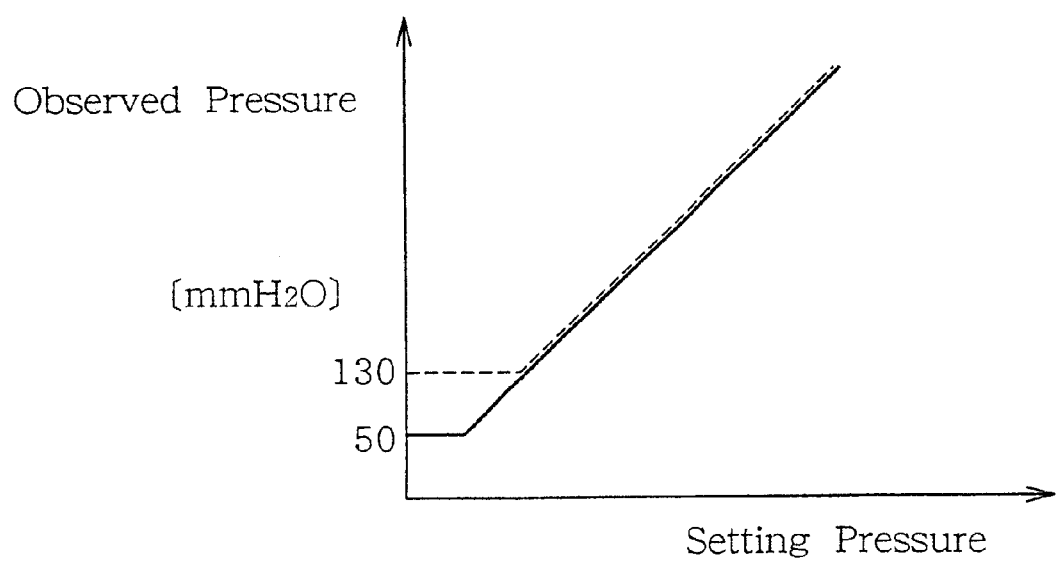
FIG. 6 shows a lower limit of the control pressure of the present embodiment compared to that of a conventional apparatus.

FIG. 6 shows a change of the average mouth pressure with respect to the pressure setting. A solid line shows observation result using the respiration apparatus 12 according to the present invention. A broken line shows observation result using a conventional respiration apparatus. When the inhaling gas supply is set to 20 liters/min., even if the pressure setting is lowered, the average mouth pressure cannot be lowered than 130 mmH$_2$O. On the other hand, in the artificial respiration apparatus 12 according to the present invention, the mouth pressure can be lowered down to 50 mmH$_2$O. That is, the artificial respiration apparatus having a one-way valve can set the mouth pressure lower than the conventional artificial respiration apparatus.

Figure 7:
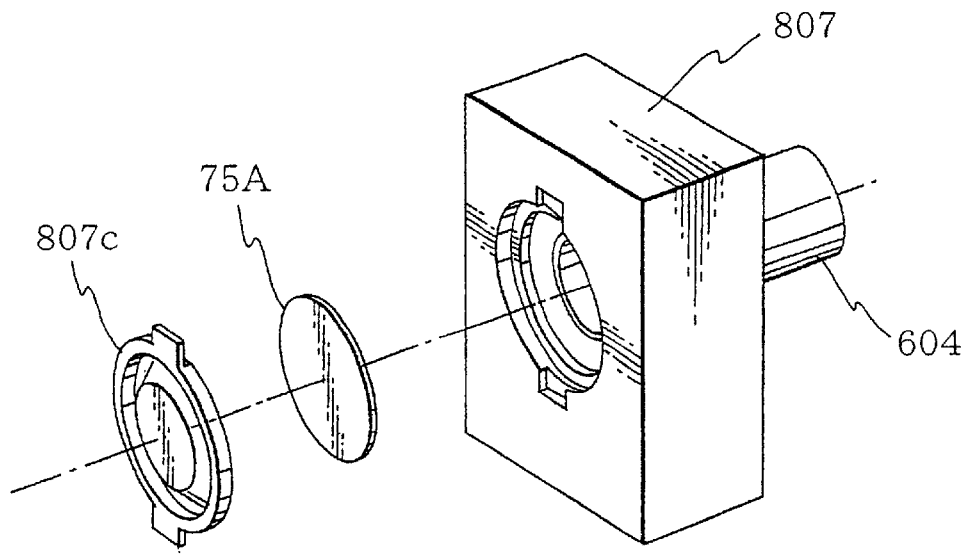
FIG. 7A is an exploded perspective view of another one-way valve and FIG. 7B is a cross sectional view of the valve members mounted.
Figure 7:
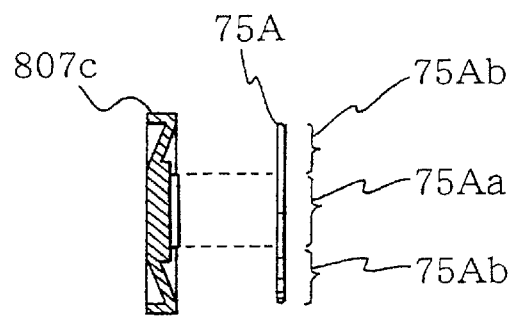

FIG. 7 shows another example of the one-way valve in which a film-shaped valve member 75A is mounted inside of the discharge valve (control silicon sheet) 807. The valve member 75A is preferably made from a rubber or resin having a high flexibility. This valve member 75A is arranged adjacent to an outlet of the discharge pipe 604. The center 75A*a* of the valve member 75A is fixed to the electromagnetic valve 807*c*.

Figure 8:
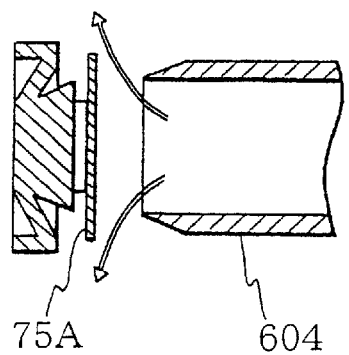
FIG. 8 is a cross sectional view of the one-way valve of FIG. 7.
Figure 8:
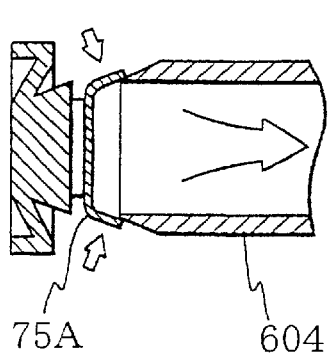
Figure 11:
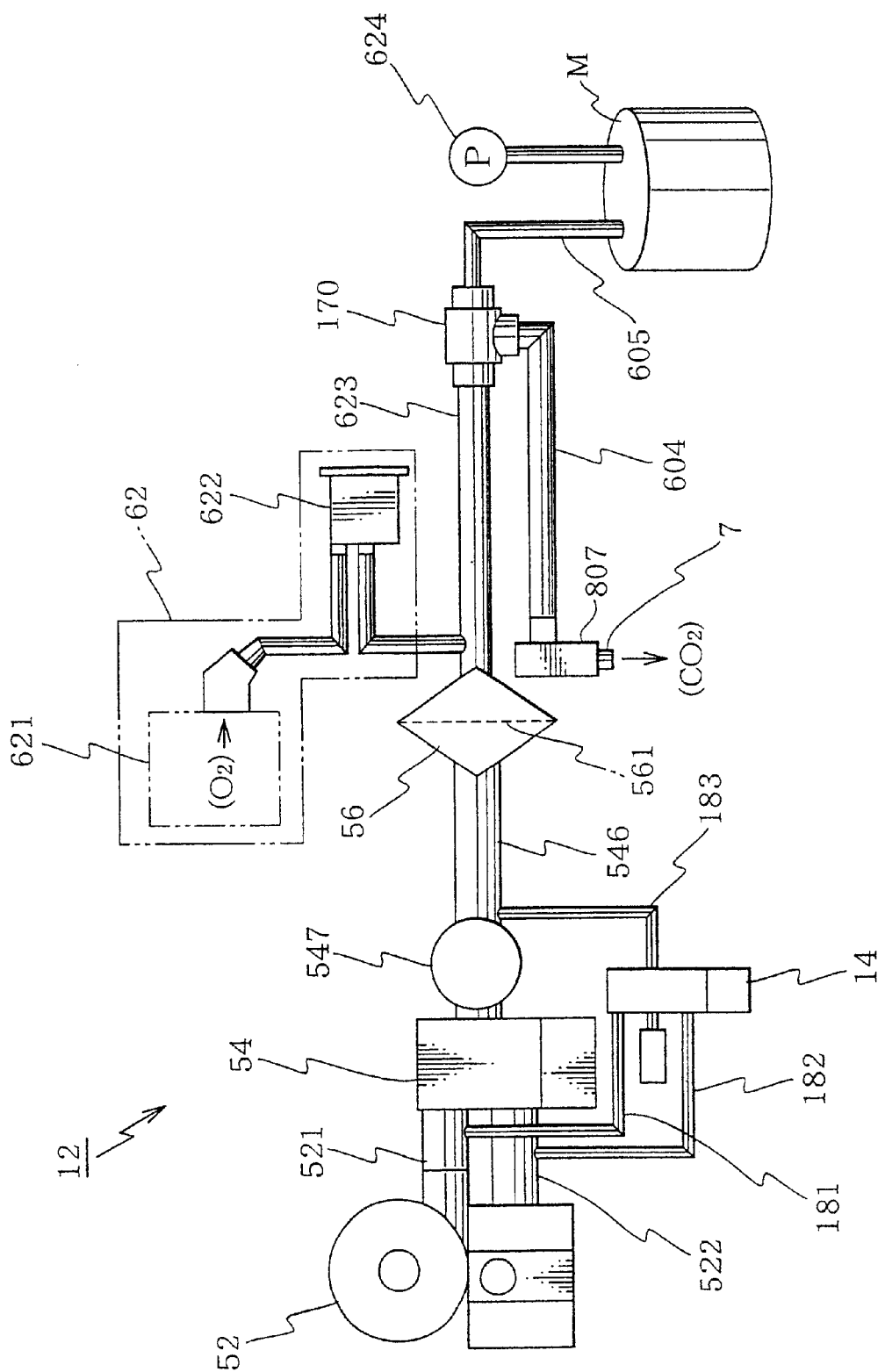
FIG. 11 shows a configuration of an artificial respiration apparatus using a lung model for test.

When the film-shaped valve member 75A is subjected to a positive pressure on the diaphragm mechanism 56, the valve member 75A maintains a normal shape as shown in FIG. 8A. That is, the exhaled gas flows out, passing through a clearance between the valve member 75A and the discharge pipe 604, as shown in FIG. 8A.

On the contrary, as shown in FIG. 5B, when a negative pressure is urged from the diaphragm mechanism 56 to the valve member 75A, its periphery 75A*b* is deformed to close the discharge pipe 604. Accordingly, no atmospheric air can intrude into the discharge pipe 604.

Thus, the valve member 75A functions in the same way as the aforementioned one-way valve. This valve member 75A can easily be added to a conventional configuration of artificial respiration apparatus. Accordingly, there is an advantage that the conventional production procedure need not be drastically changed.

FIG. 9 shows still another example of one-way valve 7B. This one-way valve is constituted by a cylindrical casing 71B and spherical valve member 75B. The cylindrical casing is connected via a connection tube 608B to the discharge port 607*b* of the discharge valve 807. Valve member 75B is contained in the cylindrical casing 71B. The cylindrical casing 71B has its center axis arranged vertically. The cylindrical casing 71B has a closed top and open bottom. That is, the bottom has a main through hole 72B for introducing the exhaled gas. This main through hole 72B is connected to the aforementioned connection tube 608B. Furthermore, this cylindrical casing 71B has two side holes 73B at the lower half of the length direction. The exhaled gas introduced into the cylindrical casing 71B is discharged through these side holes 73B. The exhaled gas coming into the cylindrical casing 71B is discharged from these side holes. Note that the main hole 72B has a circular shape coaxial with the cylindrical casing 71B and a diameter smaller than the diameter of the cylindrical casing. The spherical valve member 75 has a diameter slightly smaller than the inner diameter of the cylindrical casing 71B and can move up and down in the cylindrical casing 71B. Normally, the spherical valve member 75B stay at a lower position to cover the main hole 72B.

As shown in FIG. 10A, when a positive pressure is applied from the diaphragm mechanism 56, the spherical valve member 75B is pushed upward. When the spherical valve member 75B is pushed higher than the side holes 73B, the main hole 72B communicates with the side holes so that the exhaled gas is discharged through the side holes out of the artificial respiration apparatus 12.

On the contrary, as shown in FIG. 10B, when a negative pressure is applied from the diaphragm mechanism 56, the communication tube is under a negative pressure. Accordingly, the spherical valve member 75B is moved to its lower position to cover the bottom. This prevents intrusion of the atmospheric air through the one way valve 7B.

Thus, the one-way valve 7B has the same effect as the aforementioned one-way valve 7. Furthermore, the one-way valve 7B is constituted as a separate body from the discharge valve 607. This facilitates maintenance.

EXAMPLE

Referring to FIG. 11 to FIG. 15, a specific example of the present embodiment will be explained in comparison with a conventional artificial respiration apparatus having no one-way valve. This comparison was made using a lung model (see FIG. 11) which has means for supplying a predetermined amount of carbon dioxide.

FIG. 12 shows a flow rate distribution inside the three-way pipe 170 when subjected to a positive pressure from the diaphragm mechanism 56. FIG. 12A shows a case having no one-way valve, and FIG. 12B shows the case of the artificial respiration apparatus 12 having a one-way valve 7.

As shown in FIG. 12A compared to FIG. 12B, when no one-way valve is provided, the inhaling gas tends to flow into the discharge valve 807 rather than into the lung model M. When the one-way valve 7 is provided, the inhaling gas flows into both of the lung model M and into the discharge valve 807. It can be seen that the one-way valve suppresses the flow toward the discharge valve 607, which in turn increases the flow into the lung model M.

Figure 13:
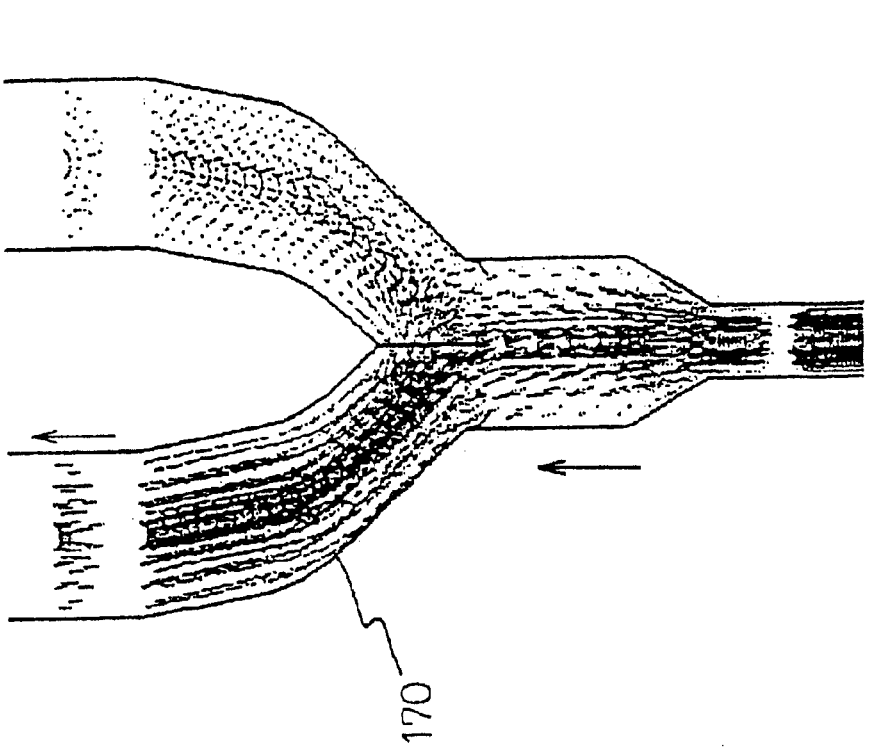
FIG. 13 shows a gas flow speed distribution in the three-way branched pipe at a negative pressure in the artificial respiration apparatus using the lung model.
Figure 13:
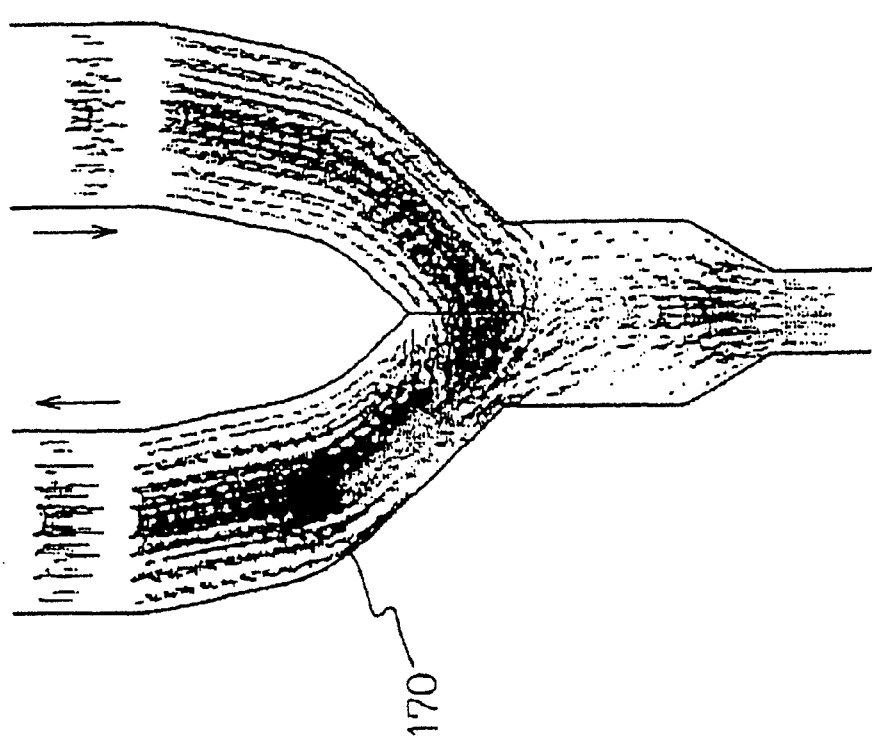

FIG. 13 shows a flow rate distribution inside the three-way pipe 170 when subjected to a negative pressure from the diaphragm mechanism 56. FIG. 13A shows a case having no one-way valve, and FIG. 13B shows the case of the artificial respiration apparatus 12 having a one-way valve 7.

As shown in FIG. 13A compared to FIG. 13B, when no one-way valve is provided, a plenty of atmospheric air flows into the discharge valve 807 and a volume of exhaled gas from the lung model is decreased. On the other hand, in the case of the artificial respiration apparatus 12 having the one-way valve 7, almost no atmospheric air flows into the apparatus, and discharge of the exhaled gas from the lung model is performed preferably.

Figure 14:
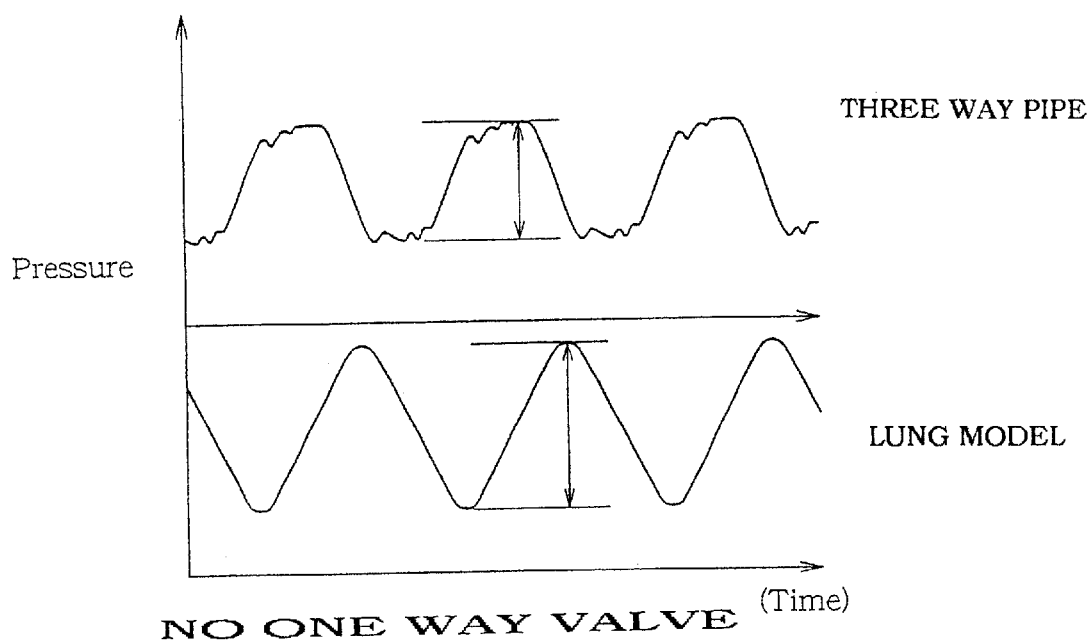
FIG. 14 is a graph showing a pressure change during a small time interval in the three-way branched pipe and the in the lung model of the artificial respiration apparatus having no one-way valve.

FIG. 14 shows an inner pressure change (only three cycles) in the lung model (lower line) and in the three-way pipe (upper line) connected to an artificial respiration apparatus having no one-way valve when the oscillating air pressure is set to frequency of 15 Hz.

Figure 15:
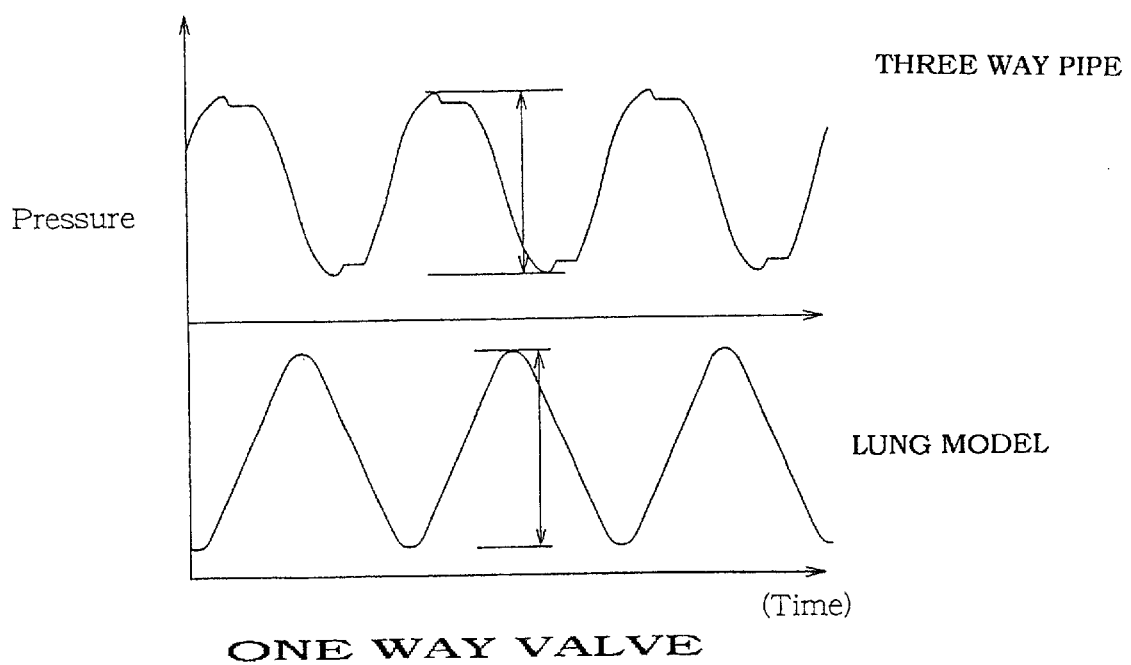
FIG. 15 is a graph showing a pressure change during a small time interval in the three-way branched pipe and the in the lung model of the artificial respiration apparatus using the one-way valve.

FIG. 15 shows an inner pressure change (only three cycles) in the lung model (lower line) and in the three-way pipe (upper line) connected to the artificial respiration apparatus having the one-way valve when the oscillating air pressure is set to the same frequency as in FIG. 4.

From the comparison between the aforementioned cases, it can be seen that when no one-way valve is provided, pressure amplitude, i.e., a maximum pressure difference in the three-way pipe is 46 mmH$_2$O, whereas in the artificial respiration apparatus 12 having the one-way valve, the pressure amplitude is 62 mmH$_2$O. This is because, if no one-way valve is provided, during a negative pressure period, atmospheric air intrudes inside the apparatus and it is impossible to obtain a sufficiently low pressure.

The tests of FIG. 14 and FIG. 15 were followed by measurement of the exhaled gas amount. It was found that when no one-way valve is provided, the exchange amount in the lung model per one cycle was calculated as 84 cc, whereas when the one-way valve is provided, the exchange amount was calculated 103 cc. This is also because of the presence and absence of the one-way valve, without which atmospheric air intrudes into the apparatus.

[Embodiment 2]

Figure 16:
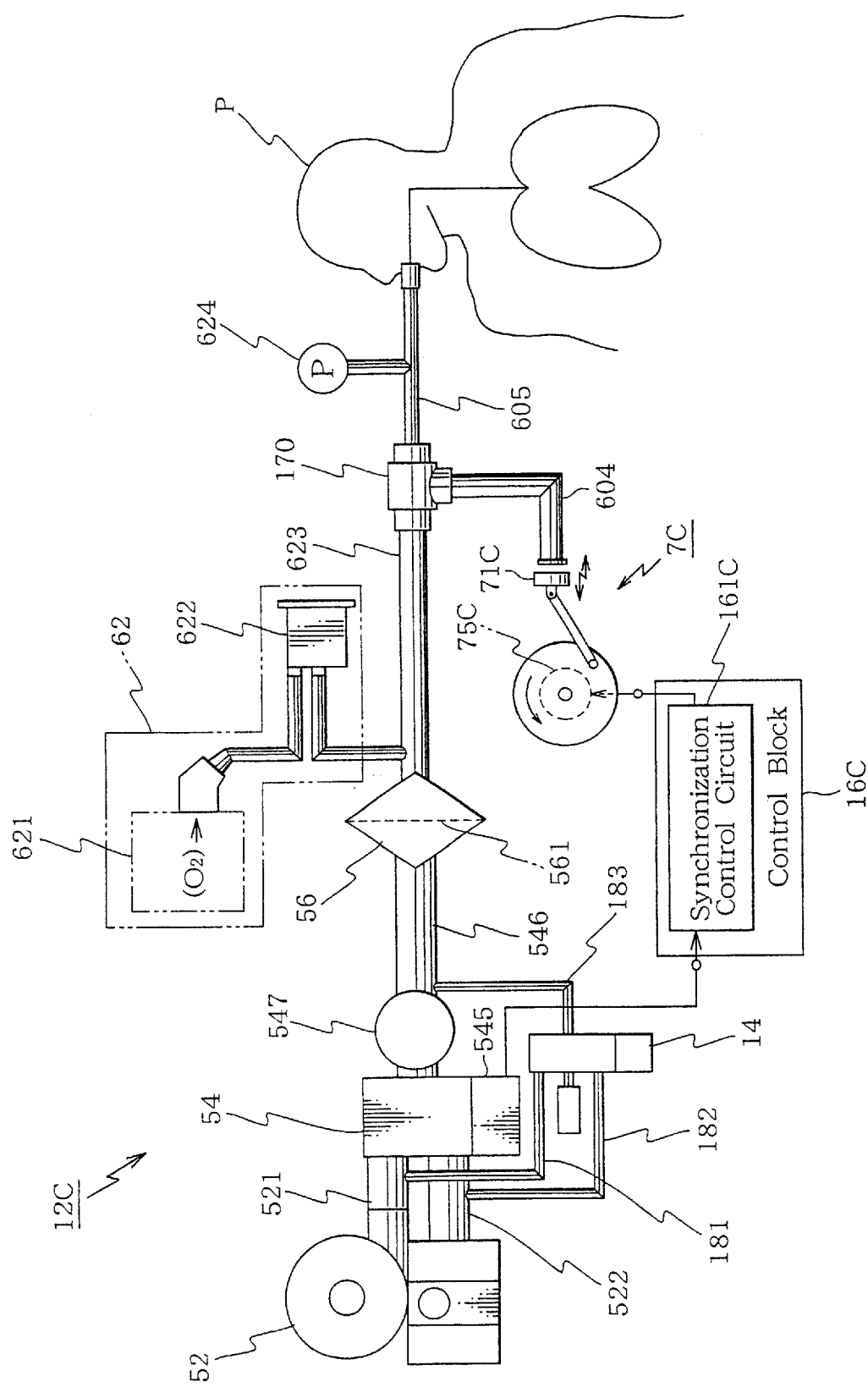
FIG. 16 shows a configuration of an artificial respiration apparatus according to a second embodiment of the present invention.
Figure 17:
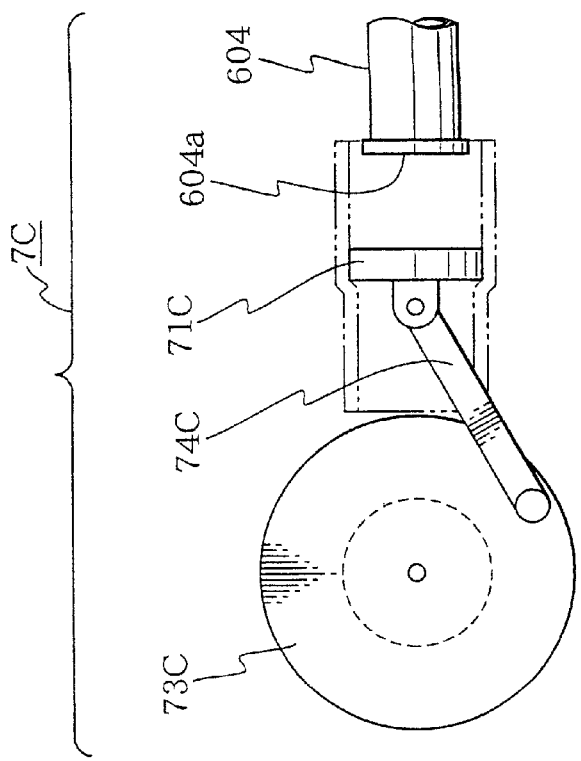
FIG. 17A shows a closed state of a switching means shown in FIG. 16.
FIG. 17B shows an open state of the switching means shown in FIG. 16.
Figure 17:
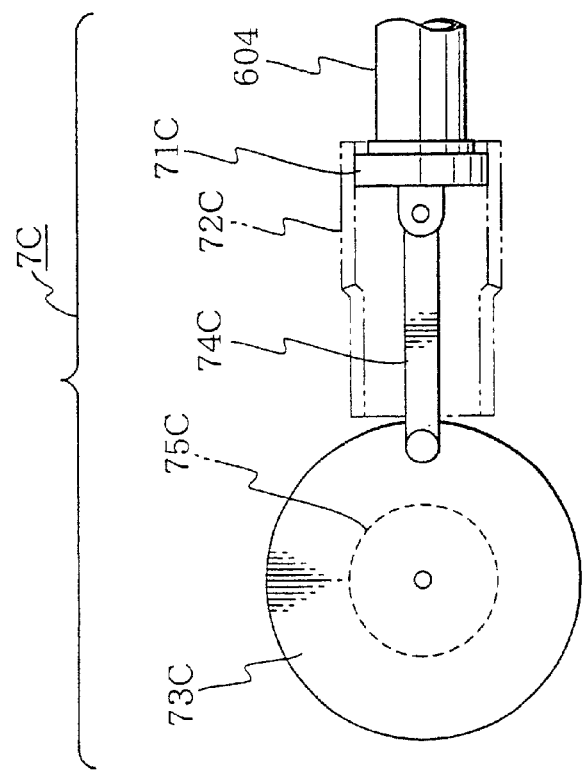

Description will now be directed to a second embodiment of the present invention with reference to FIG. 16 and FIG. 17.

The artificial respiration apparatus 12C according to the second embodiment is identical to the artificial respiration apparatus 12 of the first embodiment except for that switching means 7C is provided instead of the one-way valve and the discharge valve 807.

The switching means 7C is constituted by a cover member 71C and a crank mechanism. The cover member 71C is located at the discharge end 604a of the discharge pipe 604. The cover member reciprocally moves so as to open and close the discharge end 604a. This cover member 71C is mounted inside a cylindrical body 72C arranged on the same axis as the discharge pipe 604 in such a manner that the cover member 71C can reciprocally move inside the cylindrical body 72C. The cover member has a circular shape having an outer diameter greater than the diameter of the discharge end 604a of the discharge pipe 604.

The cover member 71C is supported by the crank mechanism, This crank mechanism is constituted by a rotary disc 73C, a linkage bar 74C, and drive motor 75C. The rotary disc 73C functions as a crank shaft. The linkage bar 74C has one end attached to a periphery point of the rotary disc 73C and the other end attached to the back of the cover. The drive motor 75C gives a rotary force to the rotary disc.

As shown in FIG. 17A, when the linkage bar attachment point on the rotary disc is nearest to the cylindrical body 72C, the cover member 71C closes the discharge end 604a The cover member 71C has one side made from an elastic material such as rubber and resin to face the discharge end. Accordingly, when the cover member 71C is brought into contact with the discharge end 604a, it is possible to maintain a high sealing effect. This prevents intrusion of an atmospheric air through the discharge end 604a into the discharge pipe.

The drive motor of the crank mechanism is a stepping motor. Accordingly, it is possible to rotate only a necessary amount according to an external operation signal. Moreover, this artificial respiration apparatus 12C includes a synchronization control circuit 161C in addition to the aforementioned control block 16C. This synchronization control circuit 161C has a function to synchronize switching operation of the switching means 7C with a cycle of the oscillating air pressure Apn.

That is, this synchronization control circuit synchronizes the drive block 545 of the rotary valve mechanism with the drive motor 75C. Furthermore, this synchronization control circuit 161C controls the drive motor 75C at a timing when the cover member 71C closes the discharge end 604a of the discharge pipe 604 under a negative pressure.

Accordingly, in this artificial respiration apparatus 12C, when a positive pressure is generated by the diaphragm mechanism 56, the cover member 71C is apart from the discharge end 604 (FIG. 7B). Thus, exhaled gas from the patient P is discharged through the discharge pipe 604 out of the artificial respiration apparatus 12C.

Moreover, when a negative pressure is generated by the diaphragm mechanism 56, the cover member 71C closes the discharge can intrude into the discharge pipe 604. Moreover, the cover member is actively made open by the drive motor 75C, without requiring time for opening. Accordingly, it is possible to discharge more effectively than when employing; the one-way valve.

[Embodiment 3]

Figure 18:
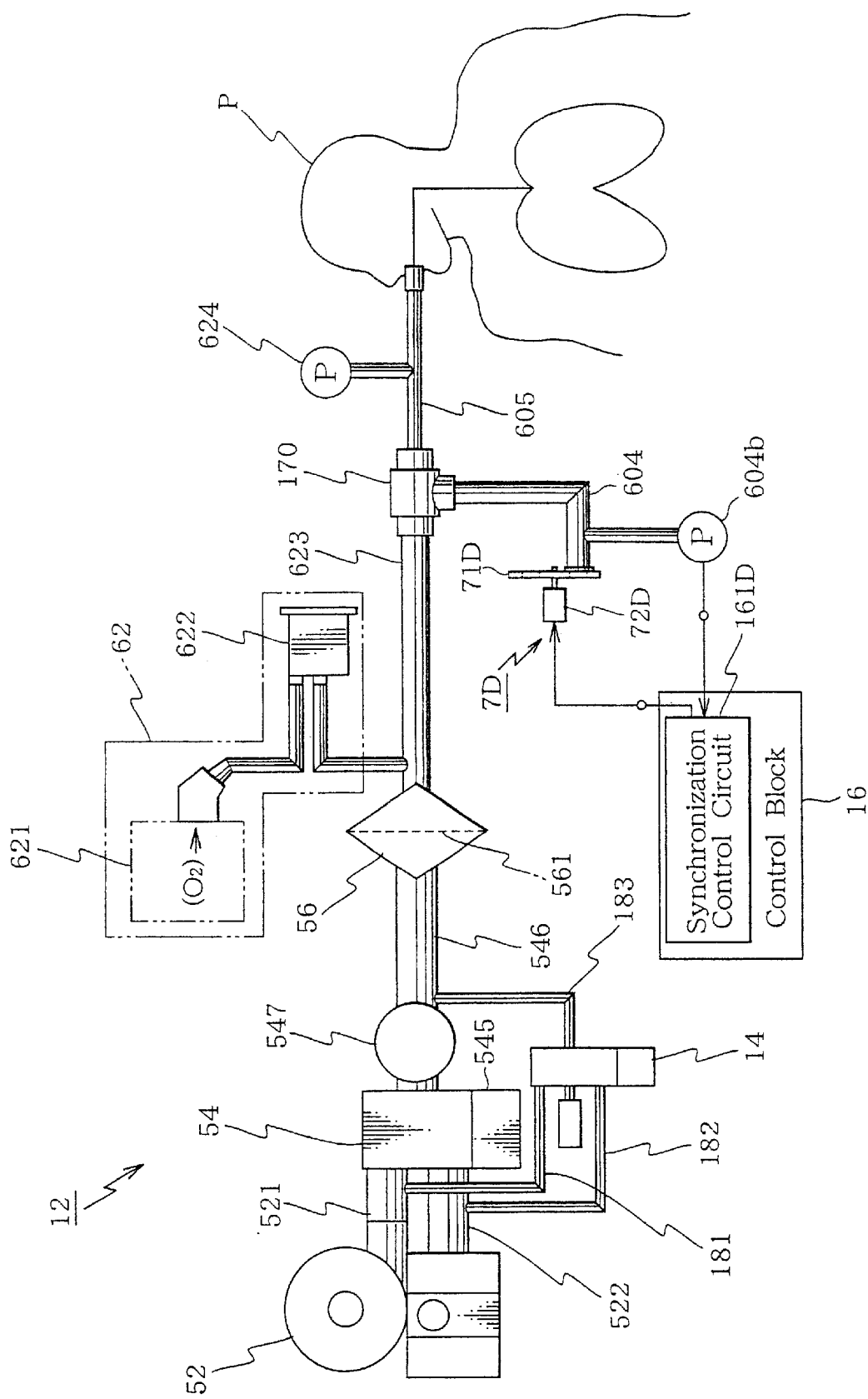
FIG. 18 shows a configuration of an artificial respiration apparatus according to a third embodiment of the present invention.

Description will now be directed to a third embodiment of the present invention with reference to FIG. 18 and FIG. 19.

The artificial respiration apparatus 12D is identical to the artificial respiration apparatus 12 except for that a discharge route open/close switching means 7D is provided instead of the one-way valve and the discharge valve 807.

The open/close switching means 7D includes a rotary plate 71D and a drive motor 72D. The rotary plate 71D has through holes 712D and a solid region 711D for closing the discharge end 604a of the discharge pipe 604. This rotary plate 71D is formed as a disc shaped and has its center fixed to the rotary axis of the drive motor 72D. This rotary plate 71D is arranged so that the discharge end 604a of the discharge pipe 604 is closed by the solid region.

The rotary plate 71D has an outer diameter greater than the outer diameter of the discharge end by two or more. Two through holes 721D are formed in this rotary plate, at symmetrical positions with respect to the center of the disc shape, and each having its center on the same circle. The remaining solid portion 711D of the rotary plate 71D serves as a discharge stop region.

The discharge end 604a is in abutment with the rotary plate 71D, with its center arranged on the aforementioned circle. Accordingly, when the rotary plate 71 is rotated by the drive motor, the through holes and the discharge stop region alternate, i.e., each time the rotary plate 71 is rotated by 90 degrees. There is almost no clearance between the discharge end 604a and the rotary plate 71D almost in a sliding state. Accordingly, when the discharge end 604a faces the discharge stop region 711D (FIG. 19A), the discharge pipe 604 is closed almost by 100%. When the discharge end 604a faces one of the through holes 712D (FIG. 19B), the discharge pipe 604 is in a completely open state.

The drive motor 72D is a stepping motor. It is possible to rotate by necessary degrees according to an external operation signal.

In the artificial respiration apparatus 12D, a pressure sensor 604b is mounted in the discharge pipe 604 for detecting the inner pressure in the discharge pipe 604.

In this artificial respiration apparatus, a synchronization control circuit 161D is added to the aforementioned control block 16. This synchronization control circuit 16 performs switching operation of the open/close switching means according to the output from the pressure sensor 604b. That is, the drive motor 75C is rotated in synchronization with the oscillating air pressure Apn detected.

When a positive pressure is detected by the pressure sensor 604b, the synchronization control circuit 161D positions one of the through holes at the position of the discharge end 604a. Next, when a negative pressure is detected by the pressure sensor 604b, the synchronization control circuit 161 positions the solid (closed) area 711D at the discharge end 604a. The oscillating air pressure Apn alternates a positive pressure and a negative pressure. According to this alternation speed, the rotary plate 71D is rotated. The drive motor 72D may be a speed control motor which is cheaper than the stepping motor.

Thus, in this artificial respiration apparatus 12D, when the discharge pipe 604 is under a positive pressure, the exhaled gas is discharged from the discharge end 712D; and when the discharge pipe is under a negative pressure, the discharge end 604a is closed by the solid (close) region 711D so as to prevent intrusion of the atmospheric air.

As has been described above, the artificial respiration apparatus, 12D can have the same effects as the aforementioned artificial respiration apparatus 12. Moreover, the pressure sensor 604b is provided immediately before the open/close switching means and according to a pressure detected by the pressure sensor 604b, it is decided to open or close the discharge pipe. This reduces a phase difference effect between the open/close switching means 7D and the pressure sensor 604. Moreover, the drive motor actively opens the discharge end 604a, not requiring much time as in the case using the one-way valve.

[Embodiment 4]

Figure 20:
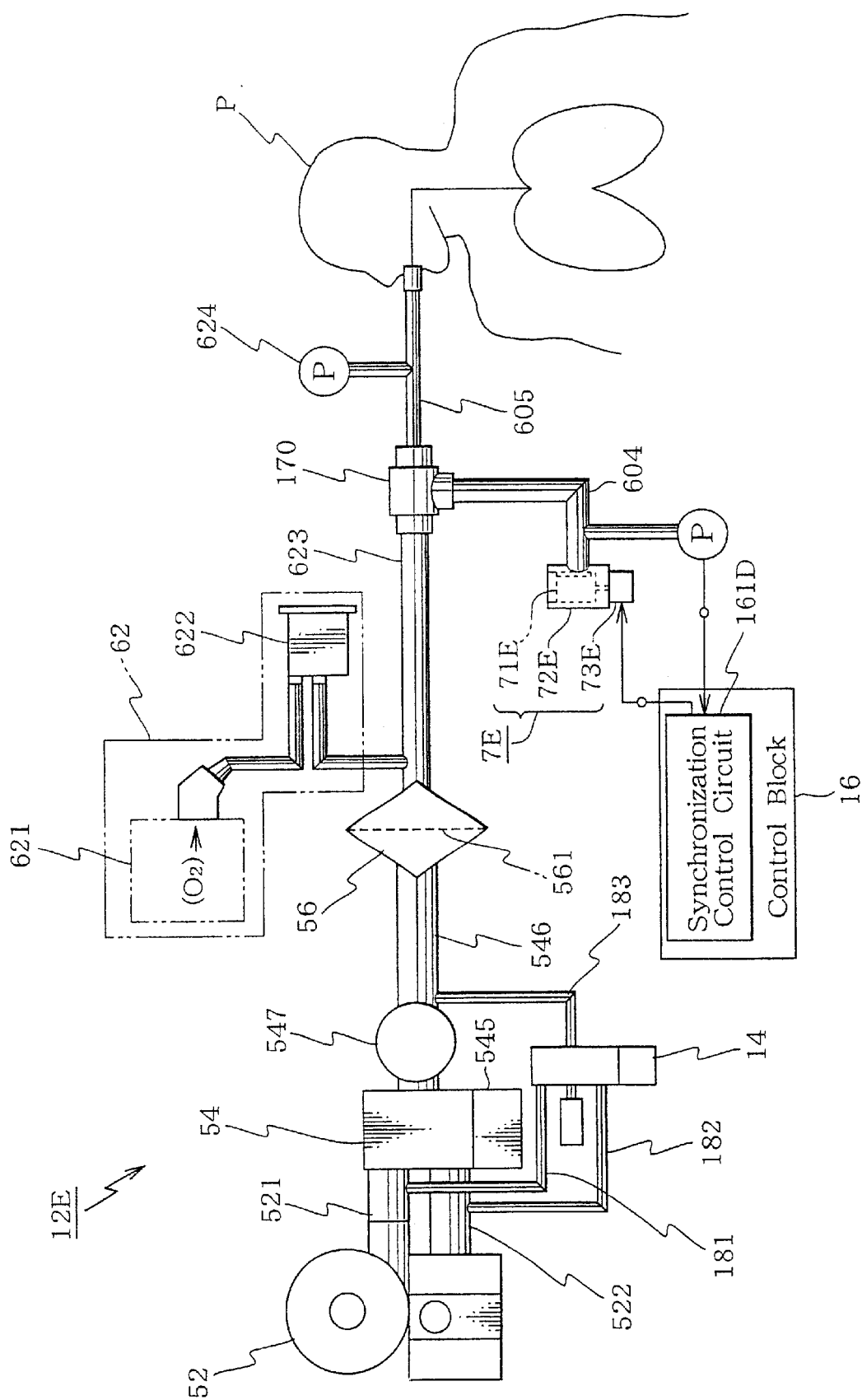
FIG. 20 shows a configuration of an artificial respiration apparatus according to a fourth embodiment of the present invention.
Figure 21A:
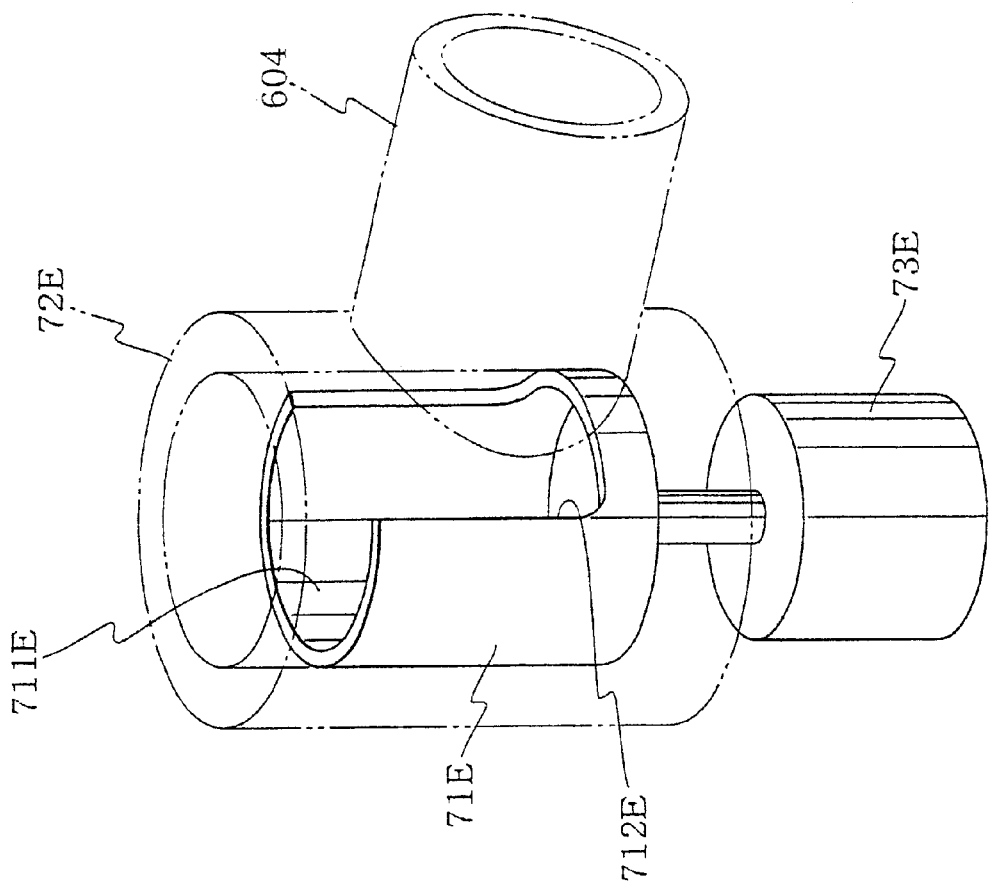
FIG. 21A shows a closed state of a switching means shown in FIG. 20.
Figure 21B:
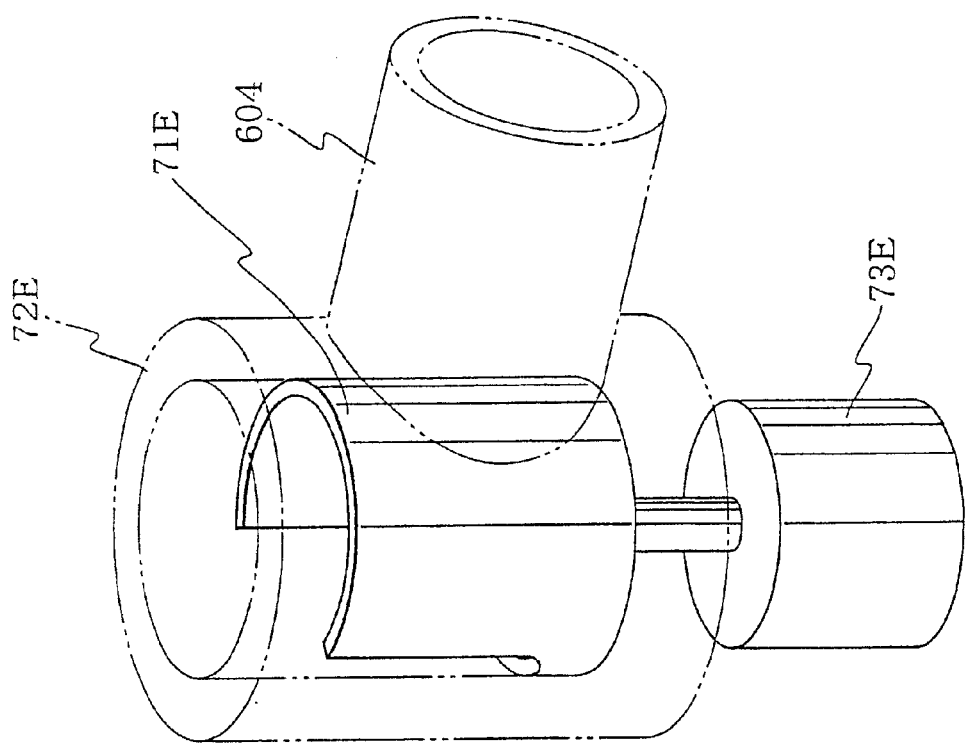
FIG. 21B shows an open state of the switching means shown in FIG. 20.
Figure 22:
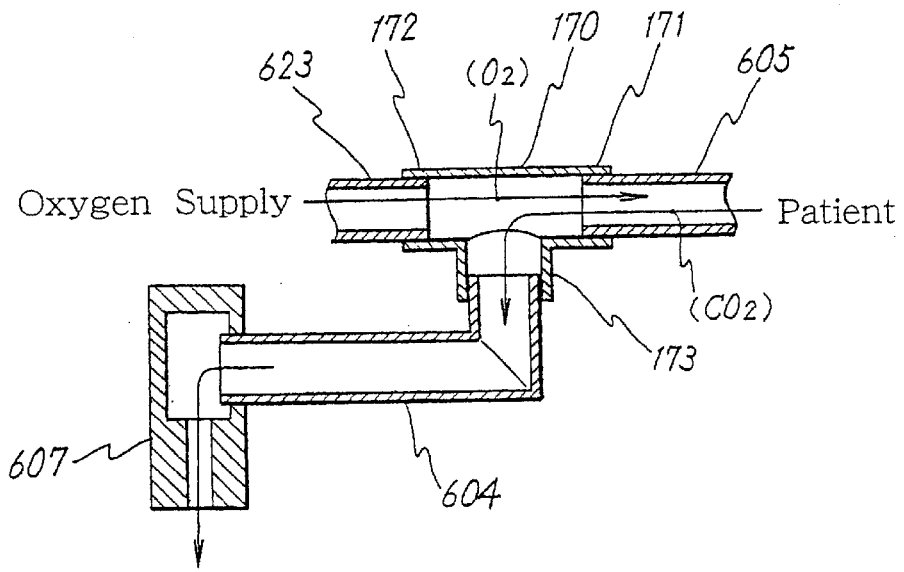
FIG. 22 is a cross sectional view showing an inhaling gas flow and exhaling gas flow in a conventional artificial respiration apparatus.
Figure 23:
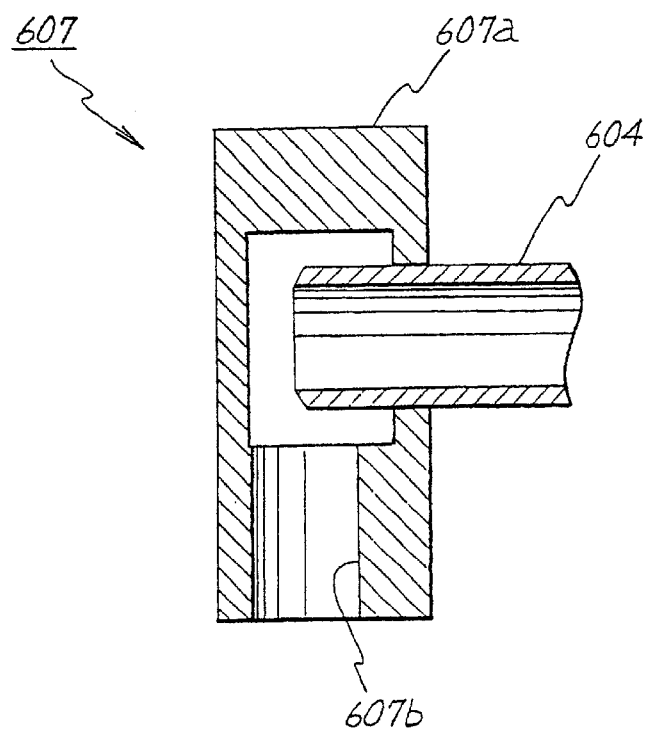
FIG. 23 is a cross sectional view of an exhaling valve in the conventional artificial respiration apparatus.
Figure 24:
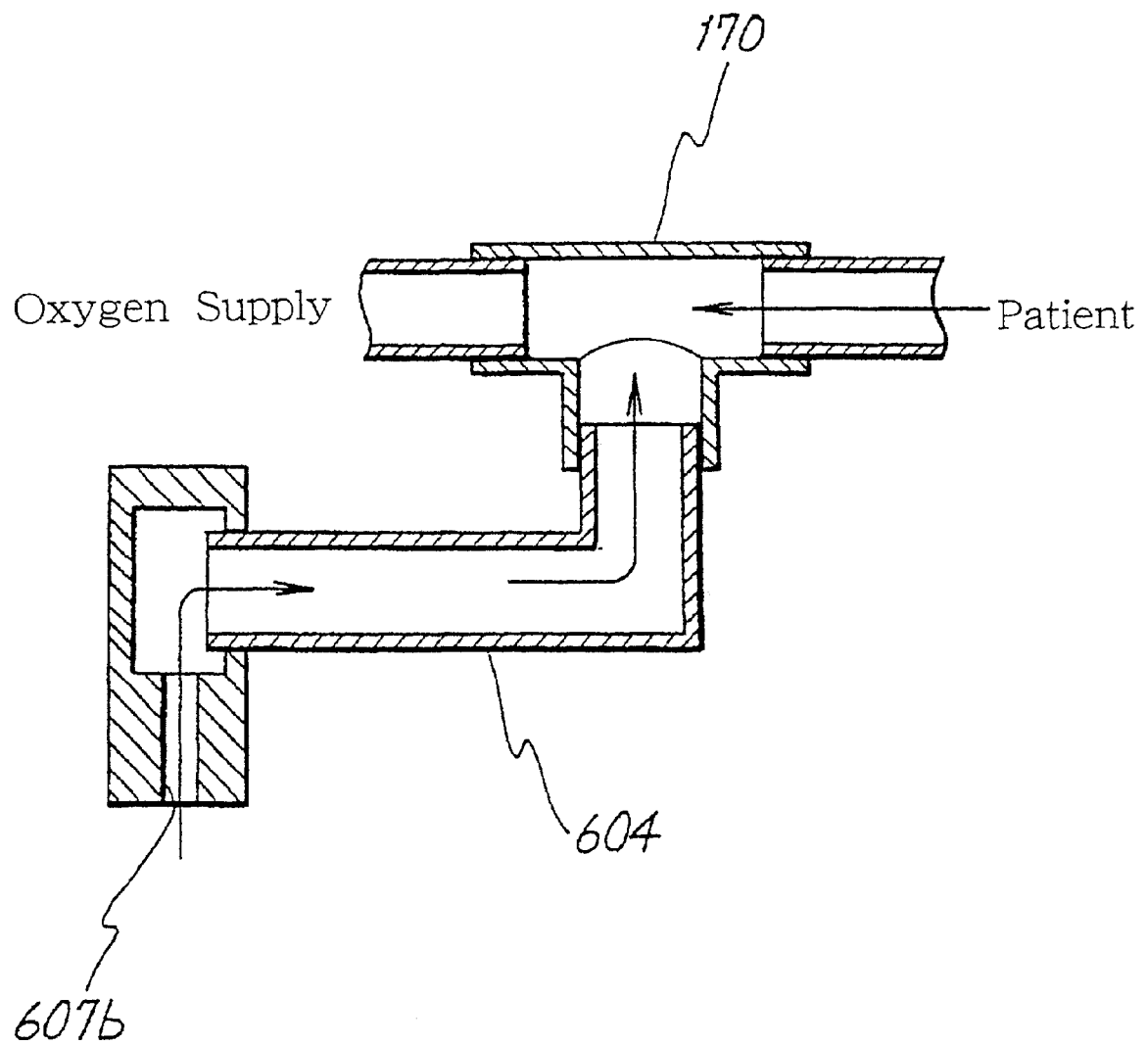
FIG. 24 is a cross sectional view of external air flowing into the conventional discharge route.

Description will now be directed to a fourth embodiment of the present invention with reference to FIG. 20 and FIG. 21.

The artificial respiration apparatus 12E according to the fourth embodiment uses another type of open/close switching means 7E instead of the one-way valve as a discharge direction regulating mechanism. This artificial respiration apparatus 12E has a configuration identical to the configuration of the artificial respiration apparatus 12 unless otherwise specified.

The open/close switching means 7E includes: a rotary cylindrical body having a cutoff portion 712E for discharge and a solid portion 711E for closing; a cylindrical frame 72E for rotatably containing this rotary cylindrical body; and a drive motor 73E for rotating the rotary cylindrical body 71E.

The cylindrical frame 72E is arranged at the discharge end of the discharge pipe 604 (see the alternate long and two short dashes line in FIG. 21). This cylindrical frame has an open top and a solid bottom. The discharge pipe 604 thrusts into the circumferential wall of the cylindrical frame 72E and communicates with the interior of the cylindrical frame 72E. Inside the cylindrical frame 72E, there is arranged the rotary cylindrical body having an outer diameter almost identical to the inner diameter of the cylindrical frame 72E, in such a manner that the rotary cylindrical body can be rotated.

The rotary cylindrical body 71E has an open top and a solid bottom like the cylindrical frame 72B, and has a cutoff portion in the circumferential wall. The position (height direction) of the rotary cylindrical body almost corresponds to the position of the discharge pipe end.

Here, in the rotary cylindrical body 71E, the cut-off portion will be referred to as an open area and the remaining portion as a closing area. The center of the bottom of this rotary cylindrical body 71E is connected to the rotary shaft of the drive motor 73E. The rotary cylindrical body 71B is rotated by the drive motor 73E with respect to the cylindrical frame 72E.

Figure 19B:
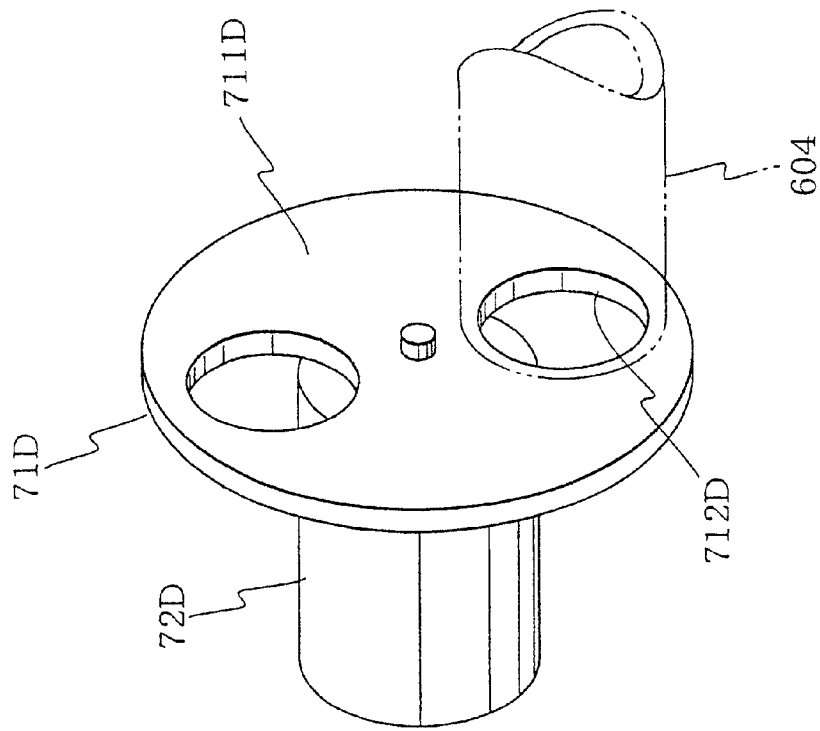
FIG. 19B shows an open state of the switching means shown in FIG. 18.
Figure 19A:
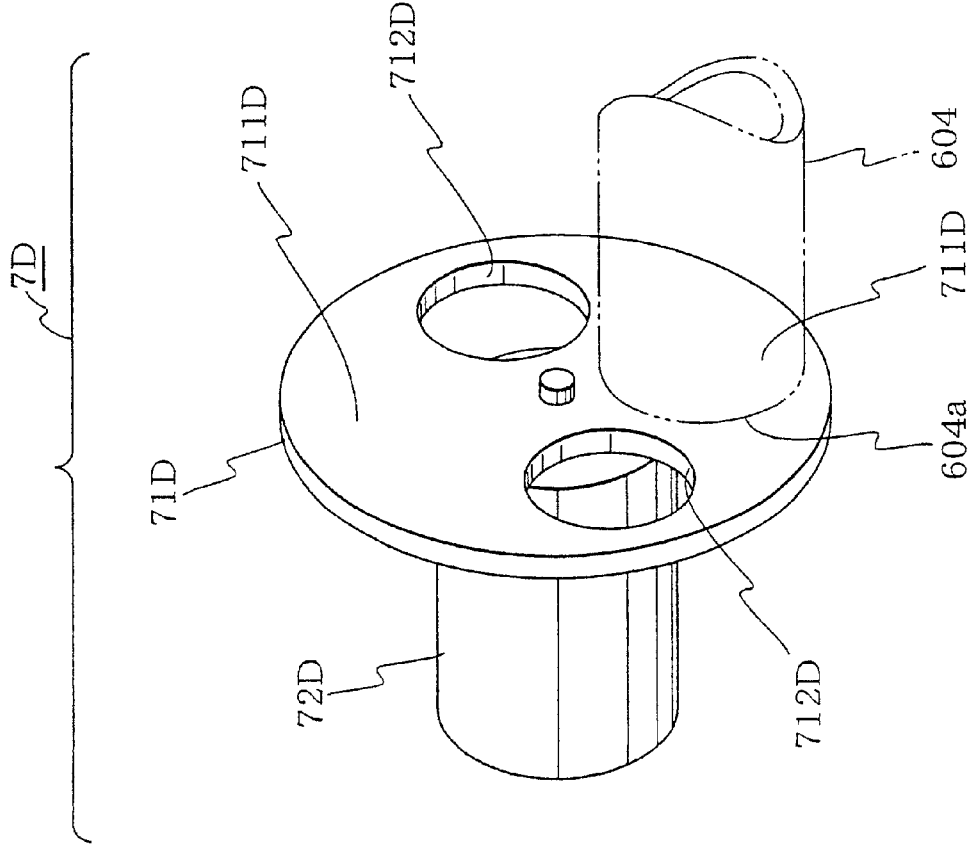
FIG. 19A shows a closed state of a switching means shown in FIG. 18.

The drive motor 73E is a stepping motor, and it is possible to rotate by an angle according to an external operation signal. Accordingly, as shown in FIG. 19A, when the closing area 711E of the rotary cylindrical body 71E is positioned to face the discharge end, the discharge pipe 604 is closed. Moreover, as shown in FIG. 19B, when the open area 712E of the rotary cylindrical body 71E is positioned to face the discharge end of the discharge pipe 604, the discharge pipe 604 can discharge the exhaled gas.

Moreover a pressure sensor 604b is mounted on the discharge pipe 604 for the control block 16 includes a synchronization control circuit 161D for synchronizing the alternation between the open and closed states of the open/close switching means 7E, with the cycle of the oscillating air pressure Apn detected by the pressure sensor 604b.

This synchronization control circuit 161D operates as follows. When a positive pressure is detected by the pressure sensor 604b, the open area 712E is positioned to face the discharge end of the discharge pipe 604. Moreover, when a negative pressure is detected by the pressure sensor 604b, the closing area 711E is positioned to face the discharge end of the discharge pipe 604. The oscillating air pressure Apn alternately applies a positive pressure and a negative pressure. According to this alternation speed, the rotary cylindrical body 71E is rotated at a predetermined speed in one direction. In this case, the drive motor 73E may be a speed control motor which costs less than the stepping motor.

Thus, in this artificial respiration apparatus 12E, when the discharge pipe 604 is under a positive pressure, the exhaled gas is discharged from the open area 712E. Moreover, when the discharge pipe 604 is under a negative pressure. The discharge end 604a is closed by the closing area 711E. This prevents intrusion of the atmospheric air.

As has been described above, the artificial respiration apparatus 12E can exhibit almost identical effects as the aforementioned artificial respiration apparatus 12D.

In the artificial respiration apparatus according to the present invention having the one-way valve in the discharge route, it is possible to prevent intrusion of the atmospheric air not only during a positive pressure but also during a negative pressure of the oscillating air pressure. Accordingly, it is possible to increase the discharge amount of the exhaled air. Moreover, it is possible to increase the gas exchange amount during one cycle of the oscillating air pressure.

Moreover, the present invention prevents intrusion of the atmospheric air, the oxygen supply pressure can be set lower. Furthermore, because no atmospheric air flows in, it is possible to assure a stable discharge amount. Accordingly, even if the respiration gas supply amount is increased, it is possible to maintain the average inner pressure at a low level.

Furthermore, according to the present invention, no atmospheric air intrudes into the apparatus, it is possible to discharge a predetermined amount of exhaled gas. Accordingly, a doctor can easily set the gas exchange amount for one cycle.

When the one-way valve is constituted by a through hole forming member and a film-shaped valve member, during a positive pressure, a flow resistance is generated to open the valve member. This prevents flow out of oxygen into the discharge route and increases the amount supplied to the patient P.

Furthermore, almost the same advantages can be obtained when the present invention includes, instead of the one-way valve, the discharge direction regulating mechanism having a switch means.

Here, the synchronization control circuit is provided for synchronization of the open/close means with the oscillating air pressure, it is possible to set a phase difference between these members so as to eliminate a time lag for opening the valve like in the one-way valve. That is, the exhaled gas can be discharged rapidly.

Moreover, when the synchronization control circuit operates the open/close switching according to a pressure detected by a sensor provided immediately before the open/close switching means, it is possible to reduce a phase difference between the open/close switching means and the pressure sensor. Moreover it is possible to eliminate the time lag generated by the opening of the valve such as the one-way valve. Thus, the exhaled gas can be discharged rapidly.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. A10-230099 (Filed on Jul. 31, 1998) including specification, claims, drawings and summary are incorporated herein by reference in its entirety.

What is claimed is:

1. An artificial respiration apparatus of the high-frequency oscillation type for introducing oxygen to a patient and discharging exhaled gas from the patient by using an oscillating air pressure having a higher cycle than a respiration cycle of a patient, the apparatus comprising a discharge direction regulating mechanism provided in a discharge route for discharging the exhaled gas from the patient, in a predetermined direction into the atmosphere; and wherein the discharge direction regulating mechanism includes a one-way valve for passing the exhaled gas only in the discharge direction, said one-way valve including a through hole forming member and an imperforate film-shaped valve member to cover the through hole from a downstream side thereof; said film-shaped valve member being partially fixed in the vicinity of the through hole.

2. The artificial respiration apparatus as claimed in claim 1, wherein said one-way valve includes a nozzle for passing an exhaled gas, said film-shaped valve member being provided on a discharge end of said nozzle and having a size sufficient to cover said nozzle discharge end, and said valve member is fixed only at its center portion.

3. The artificial respiration apparatus as claimed in claim 1, wherein said one-way valve includes: a cylindrical casing having a solid bottom; a through hole formed at the bottom of the cylindrical casing for introducing an exhaled gas into the casing; a discharge hole provided at a position on the cylindrical casing for discharging the exhaled gas; and a spherical valve member moving up and down in the cylindrical casing.

4. An artificial respiration apparatus of the high-frequency oscillation type for introducing oxygen to a patient and discharging exhaled gas from the patient by using an oscillating air pressure having a higher cycle than a respiration cycle of a patient, the apparatus comprising a discharge direction regulating mechanism provided in a discharge route for discharging the exhaled gas from the patient, in a predetermined direction into the atmosphere;

wherein the discharge direction regulating mechanism includes an open/close switching means for opening and closing the discharge route.

5. The artificial respiration apparatus claimed in claim 4, the apparatus further comprising a synchronization control circuit for synchronizing the open/close switching with a cycle of the oscillating air pressure.

6. The artificial respiration apparatus as claimed in claim 5, wherein the discharge route includes a discharge end and the open/close switching means includes: an open/close cover moving toward and away from the discharge end of the discharge route; and a crank mechanism which makes the open/close cover move toward and away from the discharge end.

7. The artificial respiration apparatus as claimed in claim 5, wherein the open/close switching means includes: a rotary disc having open areas and closing areas arranged on a circumference of said disc, said open areas including through holes in said disc and said closing areas including areas on said disc without through holes; and rotation drive means for rotating the rotary disc.

8. The artificial respiration apparatus as claimed in claim 5, wherein the open/close switching means includes: a rotary cylindrical body having open areas and closing areas arranged on a circumferential surface of said cylindrical body, said open areas including a cut off portion of said cylindrical body and said closing areas including a solid portion of said cylindrical body; and rotation drive means for rotating said rotary cylindrical body.

9. The artificial respiration apparatus as claimed in claim 4, the apparatus further comprising: a sensor arranged immediately before the open/close switching means, for detecting an inner pressure of the discharge route; and a synchronization control circuit for synchronizing the open/close switching with the pressure detected by the sensor.

10. The artificial respiration apparatus as claimed in claim 9, wherein the discharge route includes a discharge end and the open/close switching means includes: an open/close cover moving toward and away from the discharge end of the discharge route; and a crank mechanism which makes the open/close cover move toward and away from the discharge end.

11. The artificial respiration apparatus as claimed in claim 9, wherein the open/close switching means includes: a rotary disc having open areas and closing areas arranged on a circumference of said disc, said open areas including through holes in said disc and said closing areas including areas on said disc without through holes; and rotation drive means for rotating the rotary disc.

12. The artificial respiration apparatus as claimed in claim 9, wherein the open/close switching means includes: a rotary cylindrical body having open areas and closing areas arranged on a circumferential surface of said cylindrical body, said open areas including a cut off portion of said cylindrical body and said closing areas including a solid portion of said cylindrical body; and rotation drive means for rotating said rotary cylindrical body.

13. The artificial respiration apparatus as claimed in claim 4, wherein the discharge route includes a discharge end and the open/close switching means includes: an open/close cover moving toward and away from the discharge end of the discharge route; and a crank mechanism which makes the open/close cover move toward and away from the discharge end.

14. The artificial respiration apparatus as claimed in claim 4, wherein the open/close switching means includes: a rotary disc having open areas and closing areas arranged on a circumference of said disc, said open areas including through holes in said disc and said closing areas including areas on said disc without through holes; and rotation drive means for rotating the rotary disc.

15. The artificial respiration apparatus as claimed in claim 4, wherein the open/close switching means includes: a rotary cylindrical body having open areas and closing areas arranged on a circumferential surface of said cylindrical body, said open areas including a cut off portion of said cylindrical body and said closing areas including a solid portion of said cylindrical body; and rotation drive means for rotating said rotary cylindrical body.

* * * * *